US011000356B2

(12) United States Patent
Folger et al.

(10) Patent No.: US 11,000,356 B2
(45) Date of Patent: May 11, 2021

(54) SPINAL IMPLANT PACKAGING

(71) Applicant: Warsaw Orthopedic, Inc., Warsaw, IN (US)

(72) Inventors: Leigh Anna Folger, Memphis, TN (US); David Mire, Collierville, TN (US); Caleb D. Smith, Collierville, TN (US); Christine Carmer, Memphis, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 55 days.

(21) Appl. No.: 16/225,899

(22) Filed: Dec. 19, 2018

(65) Prior Publication Data

US 2020/0197149 A1 Jun. 25, 2020

(51) Int. Cl.
*A61F 2/00* (2006.01)
*A61F 2/44* (2006.01)

(52) U.S. Cl.
CPC .............. *A61F 2/0095* (2013.01); *A61F 2/44* (2013.01)

(58) Field of Classification Search
CPC ... A61F 2/0095; A61F 2/44; B65D 2251/105; B65D 43/162; B65D 81/025
USPC ................................ 206/461–471, 738, 438
See application file for complete search history.

(56) References Cited

U.S. PATENT DOCUMENTS

| 3,869,043 | A | * | 3/1975 | Warner | B65D 75/368 206/769 |
| 3,967,730 | A | * | 7/1976 | Driscoll | B65D 75/368 206/461 |
| 4,019,633 | A | * | 4/1977 | Roth | B65D 5/503 206/364 |
| 4,210,246 | A | * | 7/1980 | Kuchenbecker | B65D 75/366 206/461 |
| 4,270,659 | A | * | 6/1981 | Kuchenbecker | B65D 75/366 206/470 |
| 4,574,951 | A | * | 3/1986 | Weaver | B65D 75/5816 206/461 |
| 4,623,336 | A | | 11/1986 | Pedicano et al. | |
| 4,681,223 | A | * | 7/1987 | Roberts | B65D 43/162 206/1.5 |
| 4,923,059 | A | | 5/1990 | Evers et al. | |
| 5,036,889 | A | | 8/1991 | Pherigo | |
| 5,067,611 | A | * | 11/1991 | Hagmann | B65D 85/24 206/383 |
| 5,154,293 | A | * | 10/1992 | Gould | B65D 75/366 206/461 |
| 5,353,929 | A | * | 10/1994 | Foster | A61B 50/33 206/364 |

(Continued)

*Primary Examiner* — Chun Hoi Cheung
(74) *Attorney, Agent, or Firm* — Sorell, Lenna & Schmidt, LLP

(57) ABSTRACT

A spinal implant package includes a tray having a body including spaced apart first and second cavities. The body includes a third cavity between the first and second cavities. The tray includes a first connecting feature that is movable relative to the body. A lid is coupled to the tray by a hinge. The lid includes a second connecting feature that is movable between a first position in which a bottom surface of the second connecting feature directly engages a top surface of the first connecting feature and a second position in which a top surface of the second connecting feature directly engages a bottom surface of the first connecting feature to provisionally fix the lid to the tray.

19 Claims, 18 Drawing Sheets

(56) References Cited

U.S. PATENT DOCUMENTS

| | | | | |
|---|---|---|---|---|
| 5,447,230 | A | * | 9/1995 | Gerondale ........... B65D 5/5002 |
| | | | | 206/363 |
| 5,485,917 | A | * | 1/1996 | Early .................... B65D 5/725 |
| | | | | 206/363 |
| D395,234 | S | * | 6/1998 | Shida ............................ D9/423 |
| 6,230,964 | B1 | * | 5/2001 | Saito ..................... B65D 75/22 |
| | | | | 206/462 |
| 8,042,690 | B2 | * | 10/2011 | Lewis .................. B65D 43/162 |
| | | | | 206/471 |
| 9,954,208 | B2 | * | 4/2018 | Dorr .................. B65D 73/0021 |
| 2013/0161344 | A1 | | 6/2013 | Park et al. |
| 2016/0001966 | A1 | * | 1/2016 | Putnam ................. B65D 77/26 |
| | | | | 206/470 |

* cited by examiner

SPINAL IMPLANT PACKAGING

TECHNICAL FIELD

The present disclosure generally relates to medical devices for the treatment of musculoskeletal disorders, and more particularly to a spinal implant system and a method for treating a spine.

BACKGROUND

Spinal pathologies and disorders such as scoliosis, kyphosis, and other curvature abnormalities, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support vertebral members. During surgical treatment, one or more rods and bone fasteners can be delivered to a surgical site. The rods may be attached via the fasteners to the exterior of two or more vertebral members. Set screws may be used to fix the rods to the fasteners. Surgical treatment may employ surgical instruments and implants that are manipulated for engagement with vertebrae to position and align one or more vertebrae. Implants, such as, for example, the fasteners, rods and set screws are typically delivered to medical personnel in molded packages. However, such packages typically require that the implants be touched by medical personnel to remove the implants from the package, thus compromising the sterility of the implants. Furthermore, such packages are often bulky and therefore result in a significant amount of medical waste. This disclosure describes an improvement over these prior technologies.

SUMMARY

In one embodiment, a spinal implant package includes a tray having a body including spaced apart first and second cavities. The body includes a third cavity between the first and second cavities. The tray includes a first connecting feature that is movable relative to the body. A lid is coupled to the tray by a hinge. The lid includes a second connecting feature that is movable between a first position in which a bottom surface of the second connecting feature directly engages a top surface of the first connecting feature and a second position in which a top surface of the second connecting feature directly engages a bottom surface of the first connecting feature to provisionally fix the lid to the tray.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

Figure 1:
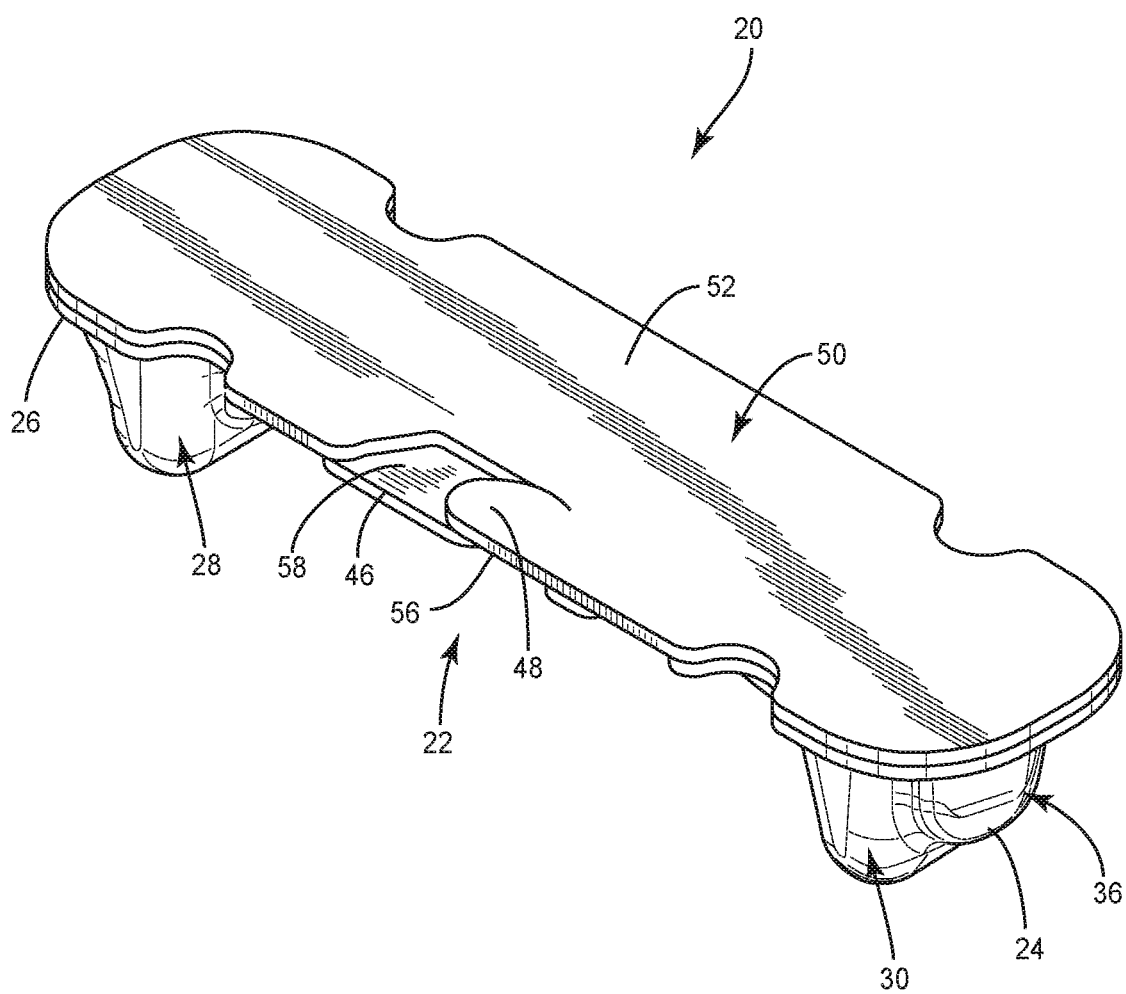
FIG. 1 is a perspective view of one embodiment of a package, in accordance with principles of the present disclosure.

The exemplary embodiments of the surgical system and related methods of use disclosed are discussed in terms of medical devices for the treatment of musculoskeletal disorders and more particularly, in terms of a spinal implant system and a method for treating a spine. In some embodiments, the systems and methods of the present disclosure comprise medical devices including surgical instruments and implants that are employed with a surgical treatment, as described herein, for example, with a cervical, thoracic, lumbar and/or sacral region of a spine.

In some embodiments, the present surgical system includes a holder or packaging that allows multiple packaging configurations of set screws and rods. The packaging may be referred to as a universal packaging or holder. In some embodiments, the packaging can hold one or a plurality of set screws and/or one or a plurality of spinal rods. For example, the package can hold a plurality of the same type of set screw or a plurality of different types of set screws and/or a plurality of the same type of spinal rod or a plurality of different type of spinal rods, wherein the setscrews differ from one another in size, shape and/or geometry and the spinal rods differ from one another in size, shape and/or geometry. In some embodiments, the package includes set screws and rods for a one-level spinal fusion procedure. In some embodiments, the package includes set screws and rods for a two-level spinal fusion procedure. In some embodiments, the package includes set screws and rods for a three-level spinal fusion procedure. The packaging also presents options for no-touch loading of implants wherein the package can be opened and the contents thereof removed from the package using only one hand, as discussed herein. Disposing multiple implants, such as, for example, multiple set screws and/or multiple spinal rods in a single package reduces the amount of packaging within the operating room, equating to a reduction in cost for both the hospital and implant manufacturer. Disposing multiple implants, such as, for example, multiple set screws and/or multiple spinal rods in a single package also reduces the environmental impact related to the discarded packaging and results in more efficient surgical flow. For example, because only one package needs to be opened for a given procedure, the surgeon can avoid spending time opening multiple packages, hence reducing the overall length of the procedure.

In some embodiments, the same packaging can be used selectively to hold any one or more of 4.75 set screws, 5.5/6.0 set screws, 4.75 rods, 5.5 rods and 6.0 rods in various implant quantities and configurations. In some embodiments, when used in a kit configuration (contains both set screws and rods), the packaging allows the user to access the rod before the set screws—aligning with the surgical flow.

In some embodiments, the universal nature of the packaging presents many economic advantages for the implant manufacturer, and so for related parties (patient, hospital, etc.). When using the packaging to house multiple implants at a time, (1) the design decreases the overall packaging material and labor costs of the implants (when compared to packing for single implants), (2) the packaging fits more implants within a single carton to maximize the amount of implants being sterilized per pallet (a constant cost), decreasing the overall sterilization cost per implant, and (3) the packaging configuration can be positioned to improve operating room efficiency for various surgical procedures while still providing the benefits of sterile packed implants. In general, since the packaging can be used to house multiple types of implants, the order quantities will be significantly higher so the price per piece should be less. Moreover, because only one package needs to be opened for a given procedure, the surgeon can avoid spending time opening multiple packages, hence reducing the overall length of the procedure.

In some embodiments, the packaging can be used to house multiple implant types and sizes of implants. It can also hold various combinations of these implants to match common surgical configuration needs. This results in less packaging per procedure—equating to a reduction in cost for both the hospital and manufacturer, while also reducing the environmental impact related to discarded packaging and more efficient surgical flow. Regardless of design variation, in case of "kit configurations" (includes both rods and set screws), the user can always access the rods first. This corresponds to the surgical steps the user will be following. Both set screws and rods can be "dumped" from the packaging or loaded directly from the packaging for a "no-touch" option.

In some embodiments, the packaging is compatible with multiple implant types and sizes. This presents opportunities for various kit combinations all using the same packaging—providing a more consistent experience for the customer as well as reducing the amount of packaging and overall cost when kitting multiple implants together.

In some embodiments, the packaging can hold four set screws AND two short rods or one long rod, such as a pre-bent rod. The package is versatile in that it can be used to house various combinations of these components—e.g., two set screws and no rod, or three set screws and two short rods, or just a long rod, etc.

In some embodiments, the packaging has shallow pockets, allowing the package to hold either set screws OR a rod, but not both. Benefits include avoiding wasted packaging material should only set screws, or only rods, be needed. The one configuration can be used for packaging set screws in one part of packaging facility, and also for packaging rods in another part of the same or another facility.

In some embodiments, the packaging can have more or less pockets. The configuration selected can be determined, for instance, by the number of screws and/or rods expected to be needed for a typical surgical procedure, or portion of a procedure. For example, a four set screw and two rod configuration can correspond to a common need to join one level (two vertebrae) of the spine (a single fusion). The package can, alternatively, be sized for a two-level procedure, by accommodating six set screws and longer rods or more shorter rods, etc., for double, triple, quad fusions.

In some embodiments, the packaging can include a clasp that is easy to release (e.g., one hand), yet strong enough to hold closed to keep the contents from easily falling out, and perhaps to promote maintenance of sufficient sterility of the contents in shipping and delivery from storage to the operating area.

In some embodiments, the packaging can include a hinge designed to simultaneously (1) provide spring to bias closed sufficiently (which can maintain sufficient capture of implants in shipping and introduction to the procedure space from storage), (2) open easy enough (e.g., quickly, smoothly, and possibly with one hand), and (3) allow removal. Variables weighted include material, thickness, and using tabs and therein number, size, location, and material of tabs. In some embodiments, the package has a perforated edge, or hinge, connecting the lid and tray. The perforated hinge or edge has any suitable number of connecting tabs, such as five connecting tabs. A sterile or non-sterile person could remove the lid easily by way of the perforated edge, to facilitate subsequent removal of implants in the tray. Whether the edge is perforated, even without removing the easy-to-open top, a non-sterile person can also hold the top back, and the physician can stab set screws to remove them from the packaging.

In some embodiments, the packaging can be made from soft plastic, allowing a user to, if needed, pinch or push on the bottom of the cavities, or pockets, to push or squeeze out the set screws and/or rods. Benefits include enabling transferal of the components to a sterile tray, mating instrument or physician without the provider touching the components.

In some embodiments, the package is hinged and both sides of the hinged package can hold surgical parts. One side can hold set screws while the other holds two long rods or four short rods, for example. In various embodiments, but not all, one or both sides of the package include a harder plastic, which may be fully or partially clear or transparent, or translucent, for instance, to allow easy identification of contents.

In some embodiments, one or all of the components of the surgical system may include disposable, peel-pack, prepacked sterile devices. In some embodiments, the components of the surgical system are configured for one-time use and are disposed after they are used one time. However, it is contemplated that one or all of the components of the surgical system may be reusable. The surgical system may be configured as a kit with multiple sized and configured components, including, for example, various set screws, rods, etc. In some embodiments, one or more of the components of the surgical system are configured to be sterilized.

In some embodiments, the disclosed packages, implants, surgical methods and systems may be alternatively employed in a surgical treatment with a patient in a prone or supine position, and/or employ various surgical approaches, including anterior, posterior, posterior mid-line, direct lateral, postero-lateral, antero-lateral approaches, etc. in any body region. The packages, implants, methods and systems of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context of the other, and are not necessarily "superior" and "inferior."

Further, as used in the specification and including the appended claims, "treating" or "treatment" of a disease or condition refers to performing a procedure to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the system in accordance with the principles of the present disclosure. Alternate embodiments are also disclosed. Reference will now be made in detail to the exemplary embodiments of the present disclosure, which are illustrated in the accompanying figures. Turning now to FIGS. 1-23, there are illustrated components of a surgical system 20 in accordance with the principles of the present disclosure.

The components of surgical system 20 can be fabricated from biologically acceptable materials suitable for medical applications, including metals, synthetic polymers, ceramics and bone material and/or their composites, depending on the particular application and/or preference of a medical practitioner. For example, the components of surgical system 20, individually or collectively, can be fabricated from materials such as stainless steel alloys, commercially pure titanium, titanium alloys, Grade 5 titanium, superelastic titanium alloys, cobaltchrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of surgical system 20 may have material composites, including the above materials, to achieve various desired characteristics such as strength, rigidity, elasticity, compliance, biomechanical performance, durability and radiolucency or imaging preference. The components of surgical system 20, individually or collectively, may also be fabricated from a heterogeneous material such as a combination of two or more of the above-described materials. The components of surgical system 20 may be monolithically formed, integrally connected or include fastening elements and/or instruments, as described herein.

Surgical system 20 includes package 22, as shown in FIGS. 1-7. Package 22 includes a tray 24 comprising a body 26 having a pocket, such as, for example, a first cavity 28 that is spaced apart from a pocket, such as, for example, a second cavity 30. Cavities 28, 30 are each configured for disposal of an implant, such as, for example, a set screw 200 and/or a set screw 202 (FIGS. 16, 17 and 20-22), as discussed herein. However, it is envisioned that cavities 28, 30 may also have other set screws disposed therein, such as, for example, other types of set screws, other size set screws, etc. In some embodiments, one or more cavities of body 26, including cavity 28 and/or cavity 30 can have at least a partially flat bottom to allow package 22 to sit confidently on a flat surface, such as, for example, an operating room tray without falling over.

Figure 5:
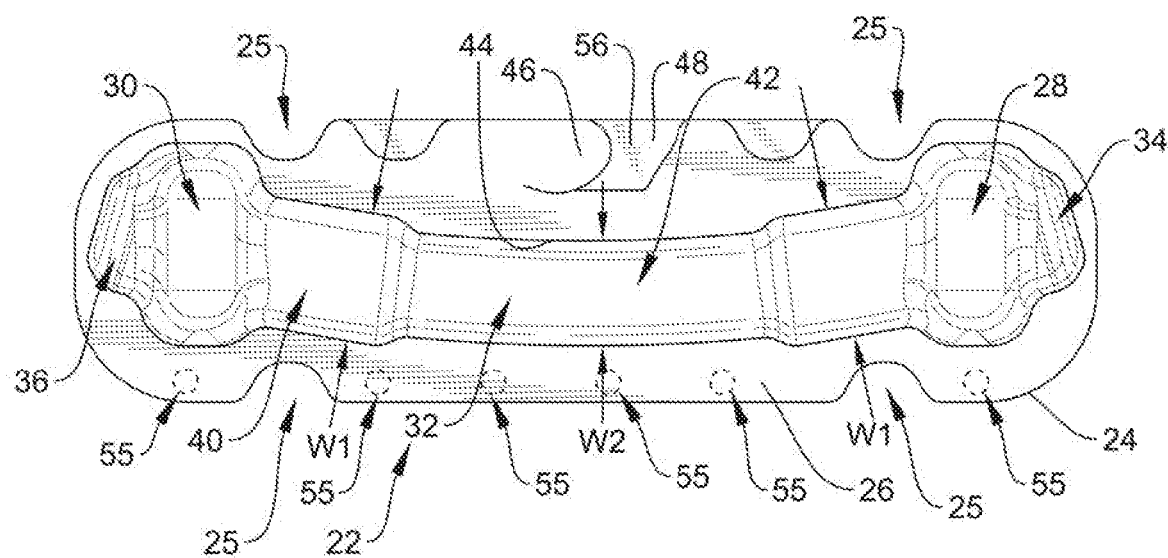
FIG. 5 is a bottom view, in part phantom, of the package shown in FIG. 1.

Body 26 comprises a pocket, such as, for example, a third cavity 32 that is positioned between cavities 28, 30. Cavity 32 is configured for disposal of an implant, such as, for example, a spinal rod 300 and/or a spinal rod 302 (FIGS. 18-22), as discussed herein. However, it is envisioned that cavities 28, 30 may also have other spinal rods disposed therein, such as, for example, other types of spinal rods, other sized diameter or length spinal rods, etc. Cavity 32 extends from cavity 28 to cavity 30 such that cavity 32 is in communication with cavities 28, 30. In some embodiments, cavity 30 is linear from cavity 28 to cavity 30 to accommodate a straight spinal rod. In some embodiments, cavity 30 is curved from cavity 28 to cavity 30, as shown in FIG. 5, to accommodate a pre-bent spinal rod. In some embodiments, cavity 30 is continuously curved from cavity 28 to cavity 30 and/or has a continuous radius of curvature from cavity 28 to cavity 30. In some embodiments, cavity 30 is curved to match the curvature of a pre-bent spinal rod. In some embodiments, body 26 includes one or a plurality of pockets that may be the same or similar to one or more of cavities 28, 30, 32 in place or, or in addition to cavities 28, 30, 32.

Figure 2:
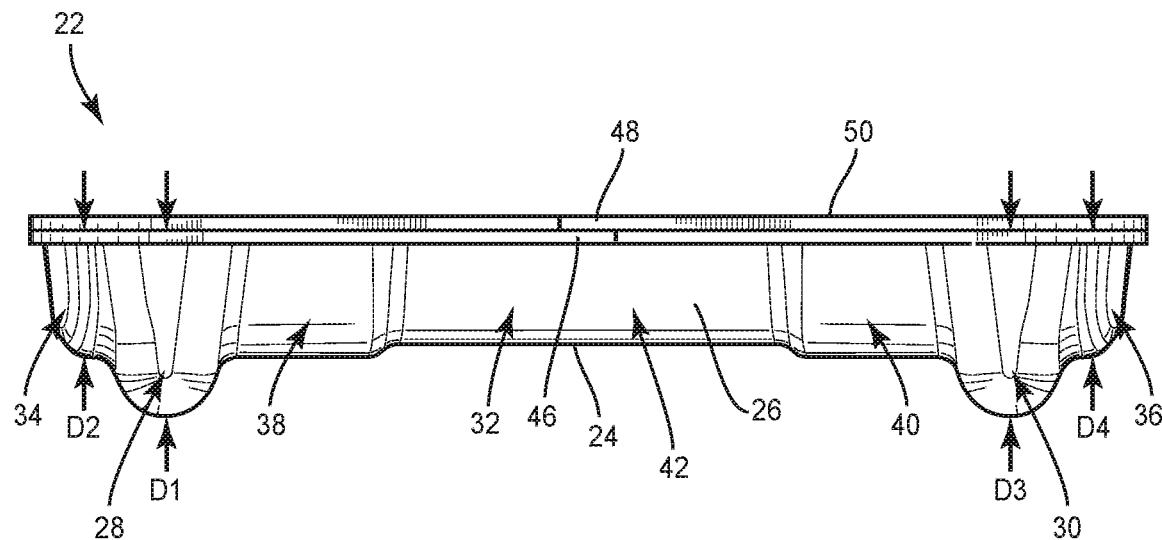
FIG. 2 is a first side view of the package shown in FIG. 1.
Figure 5A:
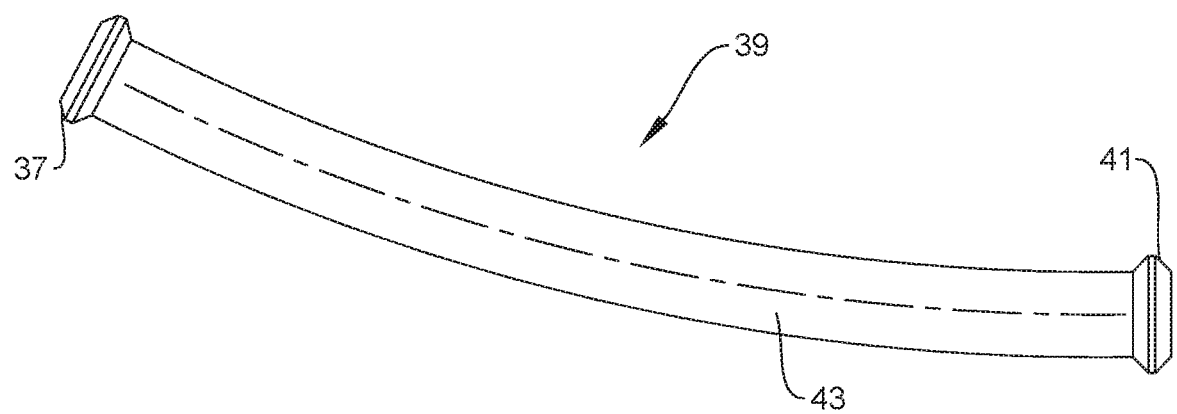
FIG. 5A is a perspective view of an implant in accordance with principles of the present disclosure.
Figure 6:
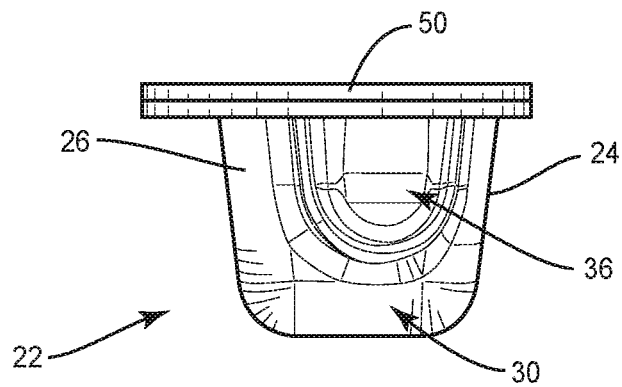
FIG. 6 is a first end view of the package shown in FIG. 1.
Figure 7:
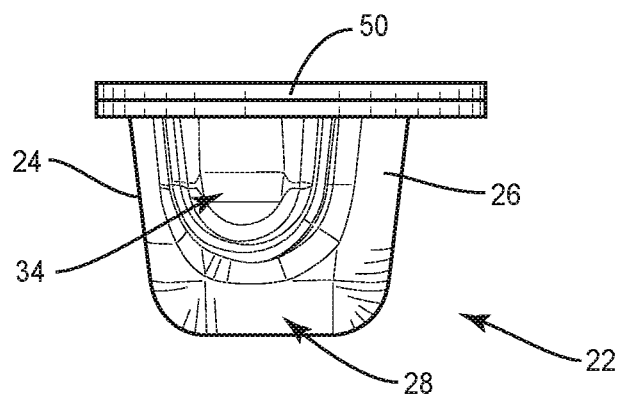
FIG. 7 is a second end view of the package shown in FIG. 1.

In some embodiments, cavity 28 includes an end portion 34 that is empty when a set screw is positioned in cavity 28. In some embodiments, portion 34 is configured for disposal of an instrument or human finger to remove a set screw from cavity 28. For example, forceps may be positioned in portion 34 to allow the forceps to grasp the set screw to remove the set screw from cavity 28. Cavity 28 has a maximum depth D1 that is greater than a maximum depth D2 of portion 34, as shown in FIG. 2. Cavity 30 includes an end portion 36 that is empty when a set screw is positioned in cavity 30. In some embodiments, portion 36 is configured for disposal of an instrument or human finger to remove a set screw from cavity 28. For example, forceps may be positioned in portion 36 to allow the forceps to grasp the set screw to remove the set screw from cavity 30. In some embodiments, portion 34 is configured for disposal of an end cap 37 of an implant, such as, for example, a spinal rod 39 (FIG. 5A) and portion 36 is configured for disposal of an end cap 41 of rod 39 when a body 43 of rod 39 is positioned in cavity 32. In some embodiments, end cap 37 is configured to directly engage an inner surface of body 26 that defines portion 34 and end cap 41 is configured to directly engage an inner surface of body 26 that defines portion 36 to prevent rod 39 from sliding and/or jostling within package 22. Cavity 30 has a maximum depth D3 that is greater than a maximum depth D4 of portion 36, as shown in FIG. 2. In some embodiments, depth D1 is equal to depth D3 to accommodate set screws of the same size in cavities 28, 30. In some embodiments, depth D1 is different than depth D3 to accommodate set screws of different sizes in cavities 28, 30. In some embodiments, depth D2 is equal to depth D4. In some embodiments, depth D2 is different than depth D4. It is envisioned that one or more of the cavities of each of the embodiments discussed herein may include end portions which are the same or similar to portions 34, 36. However, for simplicity, these features are not shown for every embodiment.

Figure 3:
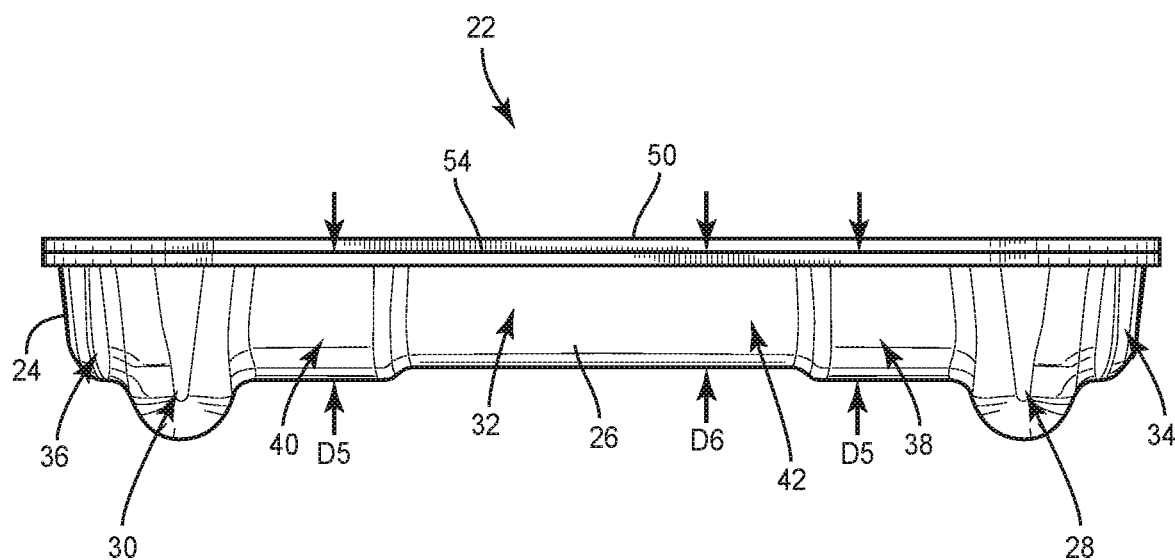
FIG. 3 is a second side view of the package shown in FIG. 1.
Figure 4:
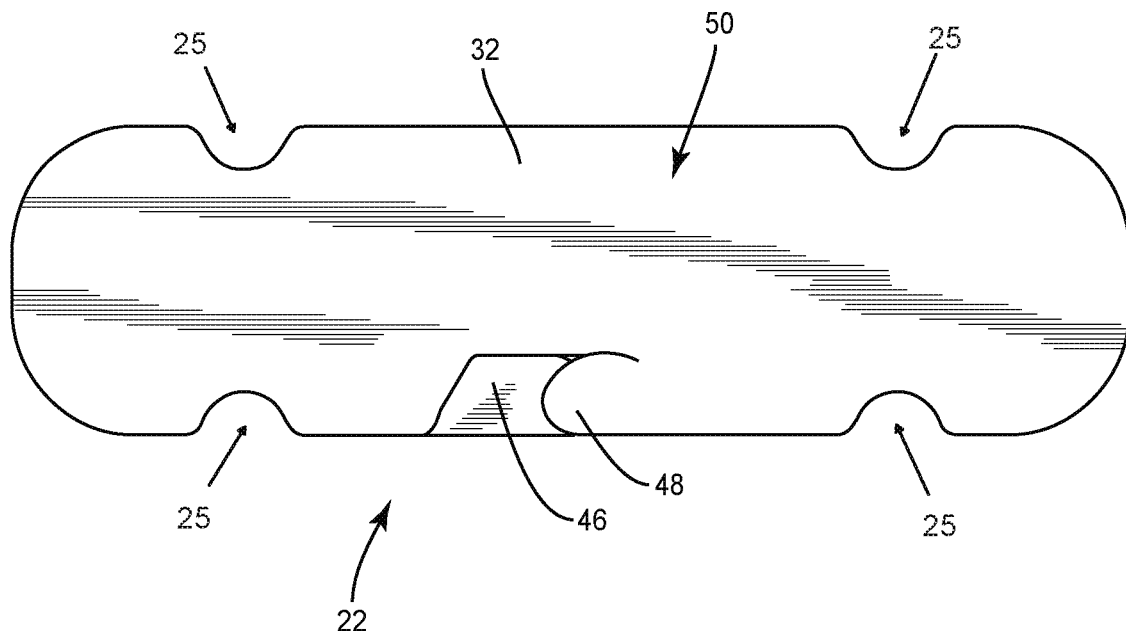
FIG. 4 is a top view of the package shown in FIG. 1.

In some embodiments, cavity 32 includes an end portion 38 that is spaced apart from an end portion 40 by an intermediate portion 42. Portions 38, 40 each have a maximum width W1 that is greater than a maximum width W2 of portion 42, as shown in FIG. 5. Portions 38, 40, 42 are defined by a wall 44. Cavity 32 is configured for disposal of a spinal rod having a maximum width that is substantially similar to width W2 such that the spinal rod directly engages wall 44 in portion 42 to provisionally fix the spinal rod within cavity 32. That is, a force is required to separate the spinal rod from wall 44 to remove the spinal rod from cavity 32. When the spinal rod is disposed in cavity 32, the spinal rod is spaced apart from wall 44 in portions 38, 40. This allows an instrument, such as, for example, forceps to be positioned in portion 38 and/or portion 40 to grasp the spinal rod within portion 38 and/or portion 40. Once the spinal rod is grasped by the forceps, a medical practitioner can manipulate the forceps to provide a force to separate the spinal rod from wall 44 to remove the spinal rod from cavity 32. In some embodiments, portions 38, 40 each have a maximum depth D5 that is greater than a maximum depth D6 of portion 42, as shown in FIG. 3. In some embodiments, portion 42 has a first dimension, such as, for example width or depth, for accommodating a rod body of a rod, such as, for example, rod 300, and portions 38, 40 have a second dimension that is larger than the first dimension for accommodating a rod end cap of a rod, such as, for example, rod 300 that is larger in a dimension than the rod body. It is envisioned that this will prevent lateral movement of the end cap within cavity 32. For example, in some embodiments, the caps abut walls of portions 38, 40 to keep the rod from further sliding in that direction. This limits jostling in the package, and may make it easier for the surgeon/assistant to pick the rod from the package, such as by keeping the rod from moving as much. It is envisioned that any of the rod cavities discussed herein can include portions that are the same or similar to portions 38, 40 and a portion that is the same or similar to portion 42 and that any of the rods discussed herein can include a rod body and endcaps.

Tray 24 comprises a connecting feature, such as, for example, a first tab 46 that is movable relative to body 26. Tab 46 is configured for engagement with a connecting feature, such as, for example, a second tab 48 of a lid 50 of package 22 to secure lid 50 to tray 24 such that lid 50 covers cavities 28, 30, 32, as discussed herein. Tab 48 is movable relative to a body 52 of lid 50. Lid 50 is attached to tray 24 by a hinge 54, as best shown in FIG. 3. In some embodiments, hinge 54 is a living hinge. In some embodiments, hinge 54 is a perforated hinge comprising spaced apart points of engagement 55 (FIG. 5) that define portions of package 22 wherein lid 50 is sealed or connected with tray 24. That is, lid 50 is not connected to tray 24 between adjacent points of engagement 55. Lid 50 is rotatable relative to tray 24 about hinge 54 to allow lid 50 to move from a closed position in which lid 50 covers cavities 28, 30, 32 and an open position in which lid 50 does not cover cavities 28, 30, 32. When lid 50 is in the closed position, tabs 46, 48 may be manipulated to secure lid 50 to tray 24. In particular, tab 48 is movable relative to tab 46 between a first configuration in which a bottom surface 56 of tab 48 directly engages a top surface 58 of tab 46, as shown in FIG. 1, such that lid 50 is rotatable relative to tray 24 about hinge 54 and a second configuration in which a top surface 60 of tab 48 directly engages a bottom surface 62 of tab 48 to provisionally fix lid 50 to tray 24 such that rotation of lid 50 relative to tray 24 about hinge 54 is prevented. That is, tabs 46, 48 will remain in the second configuration until a force is applied to tab 46 and/or tab 48 to move tabs 46, 48 from the second configuration to the first configuration. When tabs 46, 48 are in the first configuration, lid 50 is free to move from the closed position to the open position. Lid 50 is prevented from moving from the closed position to the open position when tabs 46, 48 are in the second configuration. In some embodiments, tray 24 and/or lid 50 include one or a plurality of cut-outs 25 configured to facilitate gripping of package 22 to move lid 50 between the closed and opened positions. In some embodiments, package 22 acts a sterility barrier when lid 50 is in the closed position and/or when tab 48 is in the second configuration that ensures that any implants positioned within package 22 are free from viable microorganisms, for example. That is, sterile implants that are positioned within package 22 will remain sterile when lid 50 is in the closed position and/or tab 48 is in the second configuration.

In assembly, operation and use, surgical system 20 is employed to treat an affected section of vertebrae. A medical practitioner obtains access to a surgical site including the vertebrae in any appropriate manner, such as through incision and retraction of tissues. The components of surgical system 20 including package 22, one or a plurality of set screws (e.g., set screws 200 and/or set screws 202) and/or one or a plurality of spinal rods (e.g., spinal rods 300 and/or spinal rods 302) are employed to augment a surgical treatment. Package 22 can be delivered to an operating room with lid 50 in the closed position. Set screws may be positioned in cavity 28 and/or cavity 30 and/or one or a plurality of spinal rods may be positioned within cavity 32, as discussed herein. Surgical system 20 may be may be completely or partially revised, removed or replaced.

Surgical system 20 may be used with surgical methods or techniques including open surgery, mini-open surgery, minimally invasive surgery and percutaneous surgical implantation, whereby the vertebrae are accessed through a mini-incision, or sleeve that provides a protected passageway to the area. Once access to the surgical site is obtained, a surgical treatment, for example, corpectomy and/or discectomy, can be performed for treating a spine disorder.

Surgical system 20 can include one or a plurality of bone fasteners and/or fixation elements, which may be employed with a single vertebral level or a plurality of vertebral levels. In some embodiments, the bone fasteners may be engaged with vertebrae in various orientations, such as, for example, series, parallel, offset, staggered and/or alternate vertebral levels. In some embodiments, the bone fasteners and/or fixation elements may include one or a plurality of multi-axial screws, sagittal angulation screws, pedicle screws, mono-axial screws, uni-planar screws, fixed screws, tissue penetrating screws, conventional screws, expanding screws, wedges, anchors, buttons, dips, snaps, friction fittings, compressive fittings, expanding rivets, staples, nails, adhesives, posts, fixation plates and/or posts.

Tabs 46, 48 are moved from the second configuration to the first configuration and lid 50 is moved from the closed position to the open position. In some embodiments, sterilized set screws positioned in cavity 28 and/or cavity 30 and/or one or a plurality of sterilized spinal rods positioned within cavity 32 is/are dumped onto a surface in the operating room, such as, for example, a sterilized surgical tray or table. In some embodiments, a sterilized set screw positioned in cavity 28 is removed from cavity 28 by positioning sterile forceps or other mating instrument, for example, a set screw driver, in portion 34 to grasp the set screw and remove the set screw from cavity 28 and/or a sterilized set screw positioned in cavity 30 is removed from cavity 30 by positioning sterile forceps or other mating instrument, for example, a set screw driver, in portion 36 to grasp the set screw and remove the set screw from cavity 30 and/or one or a plurality of sterilized spinal rods positioned within cavity 32 is/are removed from cavity 32 by positioning sterile forceps in portion 38 and/or portion 40 to grasp the spinal rod(s) and remove the spinal rod(s) from cavity 32. In some embodiments, the set screw(s) and/or spinal rod(s) is/are transferred from package 22 to a surface in the operating room, such as, for example, a sterilized surgical tray or table using sterile forceps. In some embodiments, the set screw(s) and/or spinal rod(s) is/are engaged with a mating instrument, for example, a set screw driver and/or rod gripper respectively, within package 22 and transferred to the surgeon without the provider touching any components. This prevents contamination of the sterilized setscrew(s) and/or sterilized spinal rod(s). In some embodiments, the sterilized spinal rod(s) is/are removed from cavity 32 as discussed herein and engaged with one or more bone fasteners that have been implanted in vertebrae. A sterilized set screw can then be removed from cavity 28 and/or cavity 30 as discussed herein and engaged with the bone fastener(s) to fix the spinal rod(s) relative to the bone fastener(s). In some embodiments, package 22 is discarded after the spinal rod(s) and/or set screw(s) are removed from package 22.

Figure 9:
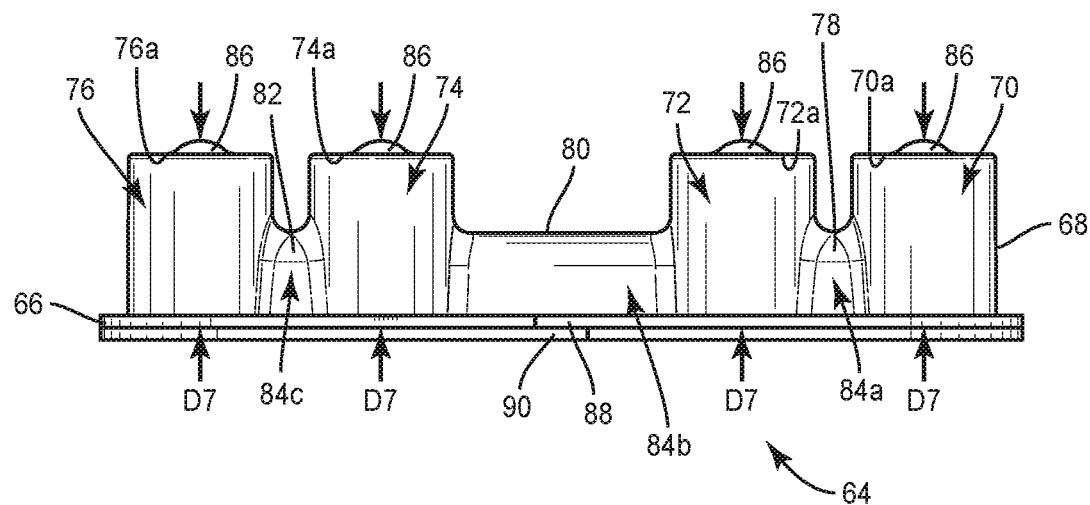
FIG. 9 is a first side view of the package shown in FIG. 8.
Figure 10:
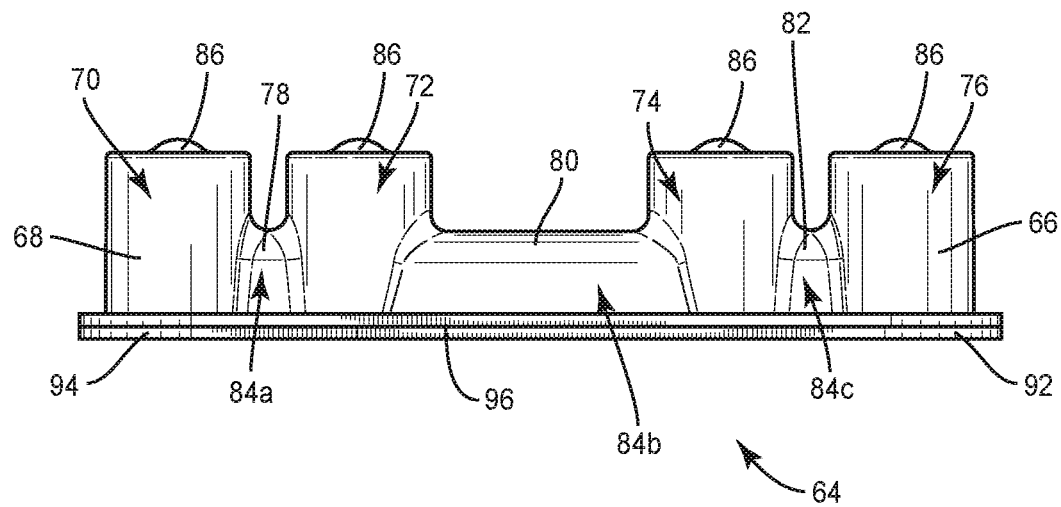
FIG. 10 is a second side view of the package shown in FIG. 8.
Figure 11:
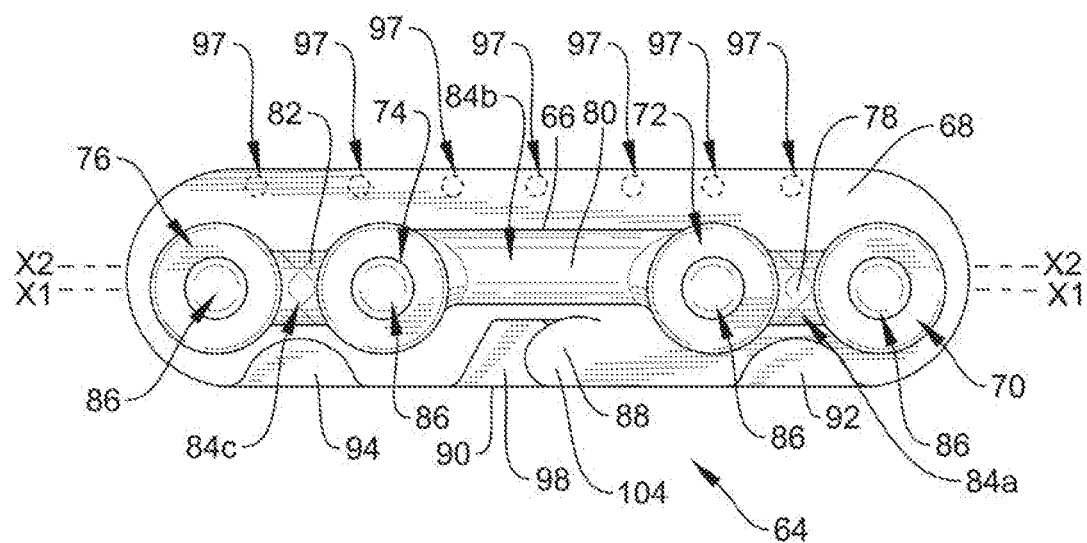
FIG. 11 is a bottom view, in part phantom, of the package shown in FIG. 8.
Figure 12:
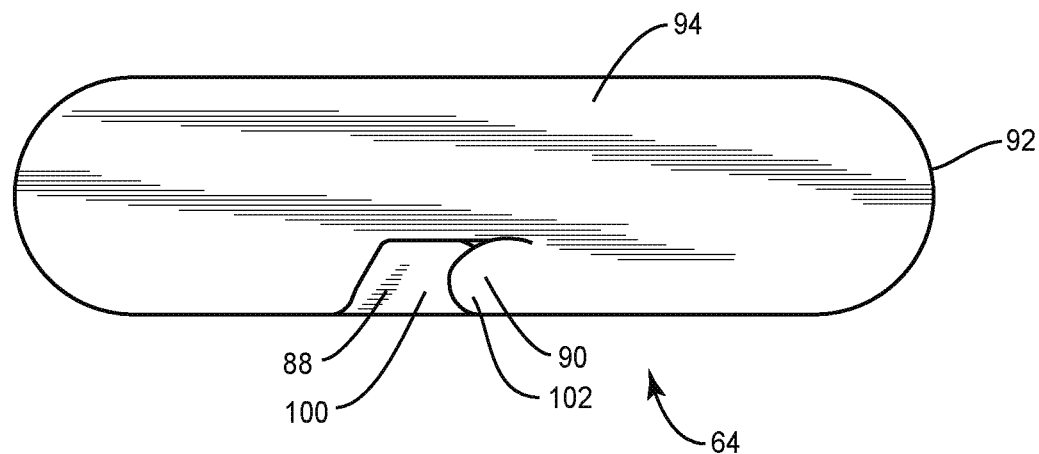
FIG. 12 is a top view of the package shown in FIG. 8.
Figure 13:
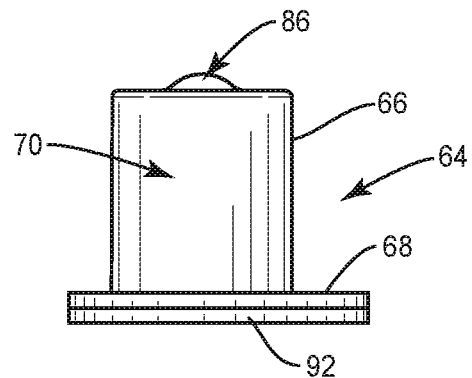
FIG. 13 is a first end view of the package shown in FIG. 8.
Figure 14:
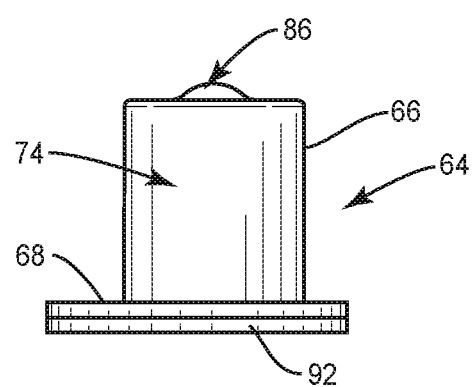
FIG. 14 is a second end view of the package shown in FIG. 8.

In one embodiment, shown in FIGS. 8-14, surgical system 20 includes a package 64 that is similar to package 22. Package 64 includes a tray 66 comprising a body 68 having pockets, such as, for example, cavities 70, 72, 74, 76. Cavities 70, 72, 74, 76 are each configured for disposal of an implant, such as, for example, set screw 200 and/or set screw 202 (FIGS. 16, 17 and 20-22). Cavity 70 is spaced apart from cavity 72 by a wall 78; cavity 72 is spaced apart from cavity 74 by a wall 80; and cavity 76 is spaced apart from cavity 74 by a wall 82. Walls 78, 80, 82 define a cavity 84 configured for disposal of an implant, such as, for example, a spinal rod 300 and/or a spinal rod 302 (FIGS. 18-22), as discussed herein. Cavity 84 extends across cavities 70, 72, 74, 76. Cavity 84 includes a portion 84a between cavities 70, 72, a portion 84b between cavities 72, 74 and a portion 84c between cavities 74, 76. In some embodiments, portions 84a, 84b, 84c are coaxial to accommodate one or more straight spinal rods within cavity 84. In some embodiments, portions 84a, 84b extend along an axis X1 and portion 84c extends along an axis X2 that is offset from axis X1, as shown in FIG. 11 to accommodate one or more pre-bent spinal rods and/or one or more straight spinal rods within cavity 84. In some embodiments, portions 84a, 84b, 84c each have an equal length. In some embodiments, portions 84*a*, 84*b* each have a length that is less than a length of portion 84*c*. In some embodiments, portion 84*b* is linear from cavity 72 to cavity 74. In some embodiments, portion 84*b* is continuously curved from cavity 72 to cavity 74 and/or has a continuous radius of curvature from cavity 72 to cavity 74.

In some embodiments, cavities 70, 72, 74, 76 each have a maximum depth D7 that is greater than a maximum depth D8 of cavity 84, as shown in FIG. 9. As such, bottom portions of cavities 70, 72, 74, 76 are positioned below a bottom portion of cavity 84. This configuration allows one or more spinal rods, such as, for example, spinal rod 300 and/or spinal rod 302 disposed in cavity 84 to be positioned above one or more set screws, such as, for example, set screws 200 that are positioned in one or more of cavities 70, 72, 74, 76 to correspond to the sequence of surgical steps. Indeed, during certain surgical procedures, a spinal rod is engaged with bone fasteners that have been implanted within a patient before set screws are engaged with the bone fasteners to fix the spinal rod to the bone fasteners, as discussed herein. As such, it is preferable to position cavity 34 above cavities 70, 72, 74, 76 so that the spinal rod can be removed from cavity 84 before the set screws are removed from cavities 70, 72, 74, 76 so as to result in an efficient surgical flow. In some embodiments, at least one of cavities 70, 72, 74, 76 has a depth that is different than at least another one of cavities 70, 72, 74, 76 to accommodate different size set screws within cavities 70, 72, 74, 76.

Figure 16:
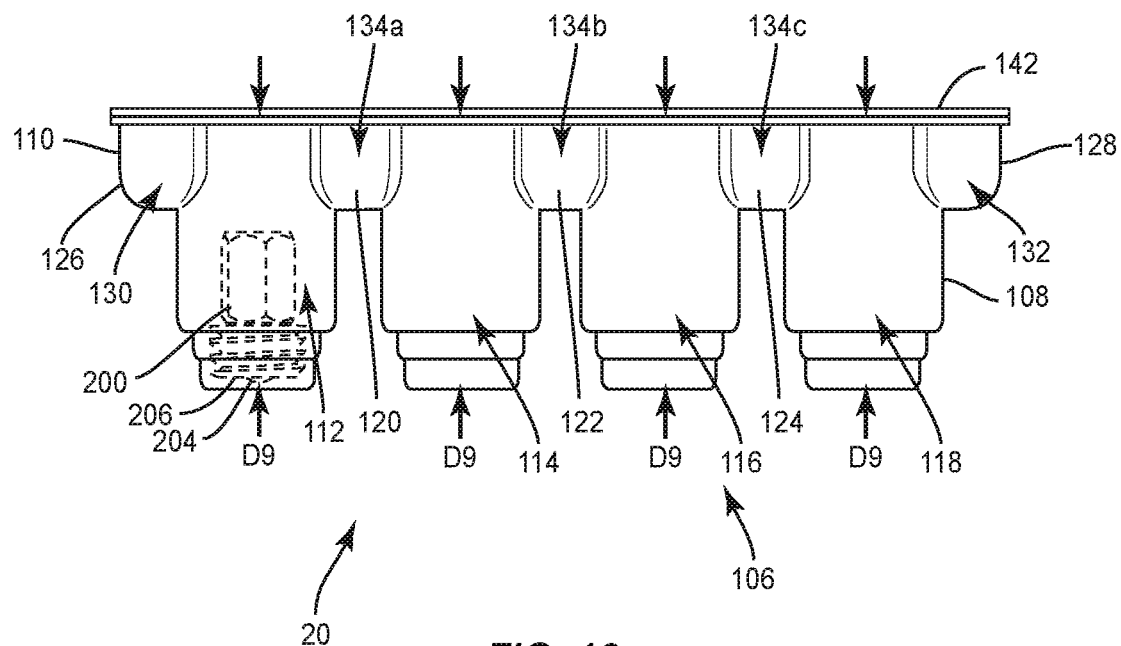
FIG. 16 is a side view, in part phantom, of the package shown in FIG. 15, with a set screw disposed therein.
Figure 17:
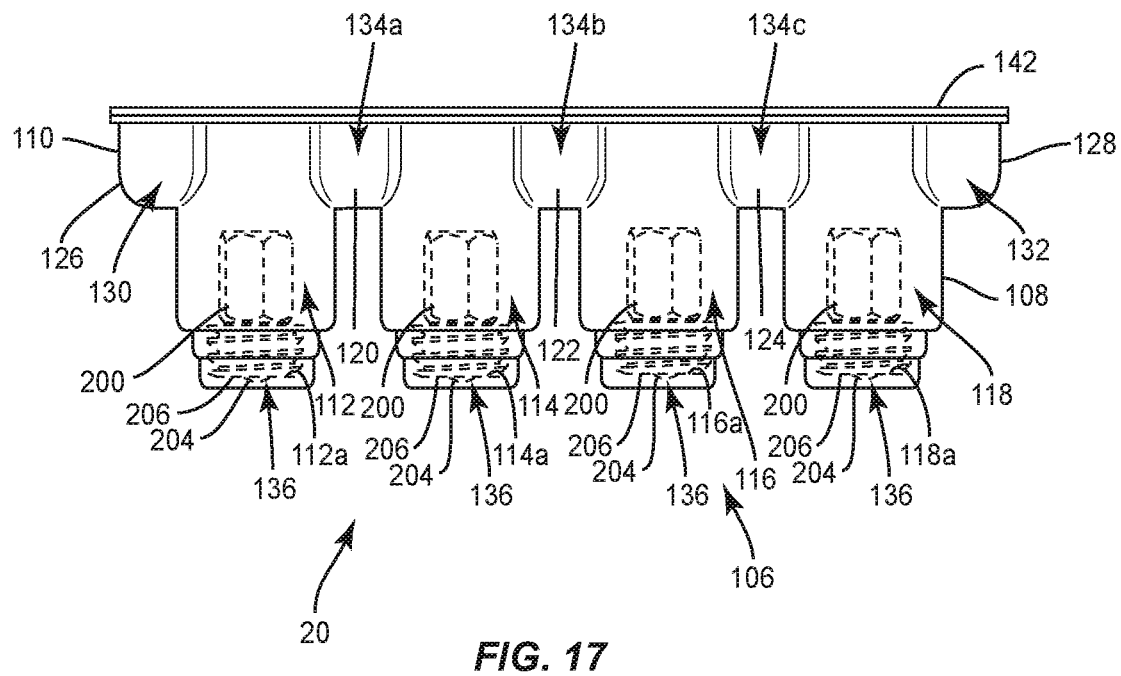
FIG. 17 is a side view, in part phantom, of the package shown in FIG. 15, with set screws disposed therein.
Figure 18:
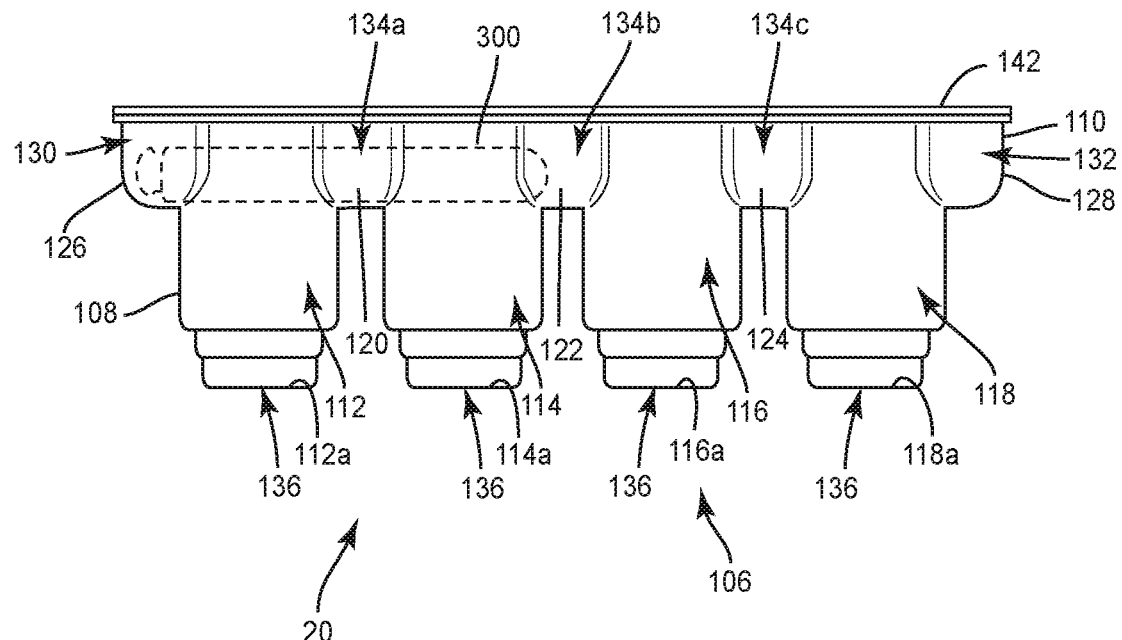
FIG. 18 is a side view, in part phantom, of the package shown in FIG. 15, with a spinal rod disposed therein.
Figure 19:
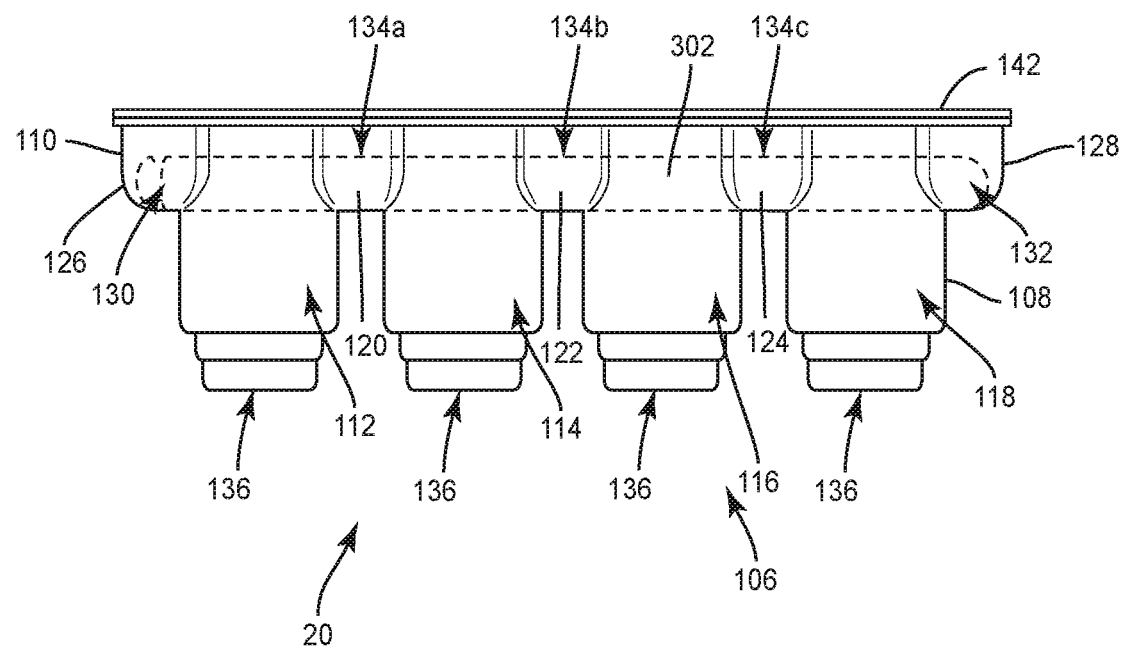
FIG. 19 is a side view, in part phantom, of the package shown in FIG. 15, with a spinal rod disposed therein.
Figure 20:
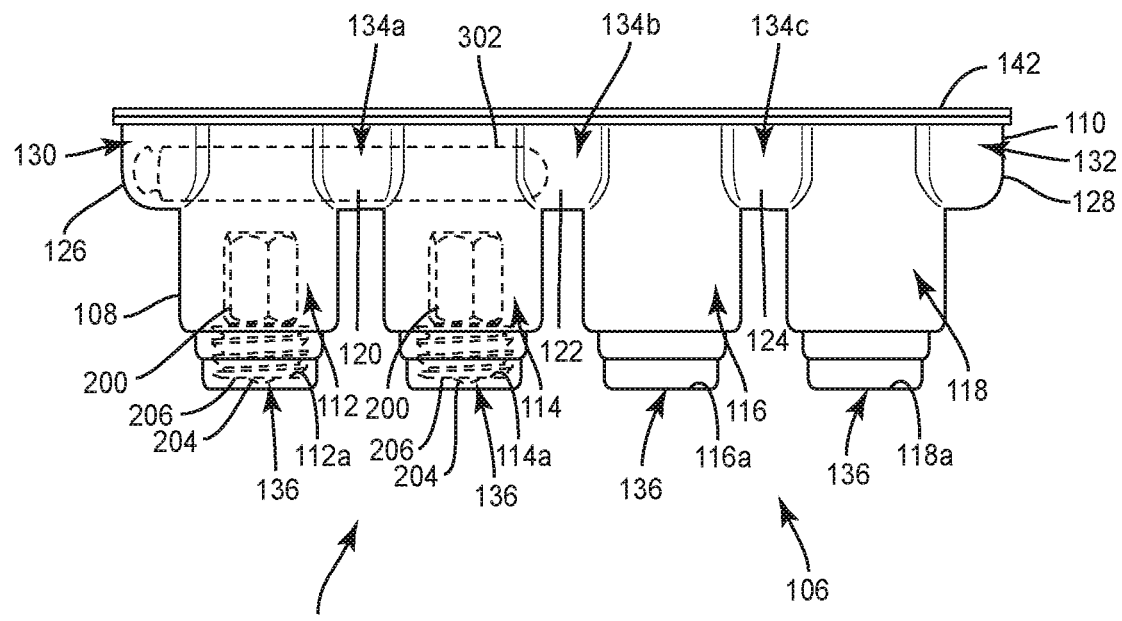
FIG. 20 is a side view, in part phantom, of the package shown in FIG. 15, with a spinal rod and set screws disposed therein.

In some embodiments, set screw 200 includes a dimple 204 that extends from a bottom surface 206 of set screw 200, as shown in FIG. 16, for example, and set screw 202 includes a dimple 208 that extends from a bottom surface 210 of set screw 202, as shown in FIG. 16, for example. Dimples 204, 208 are configured for engagement with a spinal rod, such as, for example, spinal rod 300 and/or spinal rod 302 to fix the spinal rod relative to bone fasteners that have been implanted in bone, as discussed herein. In some embodiments, dimples 204, 208 are deformable such that dimples 204, 208 deform when engaged with the spinal rod to secure set screw 200 and/or set screw 202 to the spinal rod. In some embodiments, dimples 204, 208 comprise a material that is more rigid than a material that a spinal rod, such as, for example, spinal rod 300 and/or spinal rod 302 is made from such that dimples 204, 208 deform the spinal rod when engaged with the spinal rod to secure set screw 200 and/or set screw 202 to the spinal rod.

In some embodiments, cavities 70, 72, 74, 76 each include a recess 86 configured for disposal of dimple 204 and/or dimple 208. When dimple 204 is positioned in recess 86 of cavity 70, surface 206 directly engages a surface 70*a* of body 68 to maintain set screw 200 in cavity 70 in a manner that prevents movement of set screw 200 within cavity 70. When dimple 204 is positioned in recess 86 of cavity 72, surface 206 directly engages a surface 72*a* of body 68 to maintain set screw 200 in cavity 72 in a manner that prevents movement of set screw 200 within cavity 72. When dimple 204 is positioned in recess 86 of cavity 74, surface 206 directly engages a surface 74*a* of body 68 to maintain set screw 200 in cavity 74 in a manner that prevents movement of set screw 200 within cavity 74. When dimple 204 is positioned in recess 86 of cavity 76, surface 206 directly engages a surface 76*a* of body 68 to maintain set screw 200 in cavity 76 in a manner that prevents movement of set screw 200 within cavity 76.

When dimple 208 is positioned in recess 86 of cavity 70, surface 210 directly engages surface 70*a* to maintain set screw 202 in cavity 70 in a manner that prevents movement of set screw 202 within cavity 70. When dimple 208 is positioned in recess 86 of cavity 72, surface 210 directly engages surface 72*a* to maintain set screw 202 in cavity 72 in a manner that prevents movement of set screw 202 within cavity 72. When dimple 208 is positioned in recess 86 of cavity 74, surface 210 directly engages surface 74*a* to maintain set screw 202 in cavity 74 in a manner that prevents movement of set screw 202 within cavity 74. When dimple 208 is positioned in recess 86 of cavity 76, surface 210 directly engages surface 76*a* to maintain set screw 202 in cavity 76 in a manner that prevents movement of set screw 202 within cavity 76.

Figure 8:
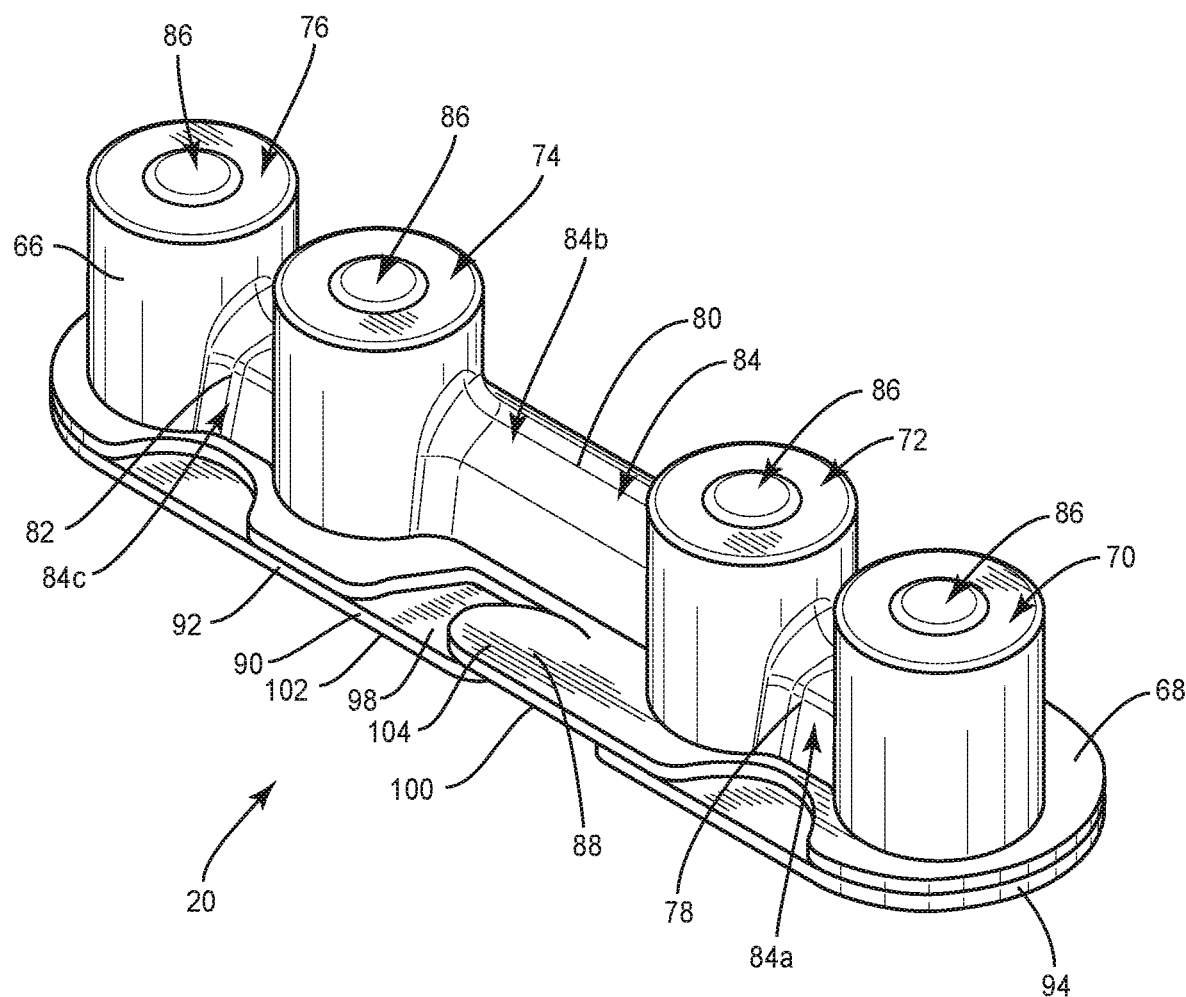
FIG. 8 is a perspective view of one embodiment of a package, in accordance with principles of the present disclosure.

Tray 66 comprises a connecting feature, such as, for example, a first tab 88 that is movable relative to body 68. Tab 88 is configured for engagement with a connecting feature, such as, for example, a second tab 90 of a lid 92 of package 64 to secure lid 92 to tray 66 such that lid 92 covers cavities 70, 72, 74, 76, 84, as discussed herein. Tab 90 is movable relative to a body 94 of lid 92. Lid 92 is attached to tray 66 by a hinge 96, as best shown in FIG. 10. In some embodiments, hinge 96 is a living hinge. In some embodiments, hinge 96 is a perforated hinge comprising spaced apart points of engagement 97 (FIG. 11) that define portions of package 64 wherein lid 92 is sealed or connected with tray 66. That is, lid 92 is not connected to tray 66 between adjacent points of engagement 97. Lid 92 is rotatable relative to tray 66 about hinge 96 to allow lid 92 to move from a closed position in which lid 92 covers cavities 70, 72, 74, 76, 84 and an open position in which lid 92 does not cover cavities 70, 72, 74, 76, 84. When lid 92 is in the closed position, tabs 88, 90 may be manipulated to secure lid 92 to tray 66. In particular, tab 90 is movable relative to tab 88 between a first configuration in which a bottom surface 98 of tab 90 directly engages a top surface 100 of tab 88, as shown in FIG. 8, such that lid 92 is rotatable relative to tray 66 about hinge 96 and a second configuration in which a top surface 102 of tab 90 directly engages a bottom surface 104 of tab 88 to provisionally fix lid 92 to tray 66 such that rotation of lid 92 relative to tray 66 about hinge 96 is prevented. That is, tabs 88, 90 will remain in the second configuration until a force is applied to tab 88 and/or tab 90 to move tabs 88, 90 from the second configuration to the first configuration. When tabs 88, 90 are in the first configuration, lid 92 is free to move from the closed position to the open position. Lid 92 is prevented from moving from the closed position to the open position when tabs 88, 90 are in the second configuration. In some embodiments, package 64 acts a sterility barrier when lid 92 is in the closed position and/or when tab 90 is in the second configuration that ensures that any implants positioned within package 64 are free from viable microorganisms, for example. That is, sterile implants that are positioned within package 64 will remain sterile when lid 92 is in the closed position and/or tab 90 is in the second configuration.

In assembly, operation and use, surgical system 20 is employed to treat an affected section of vertebrae. The components of surgical system 20 including package 64, one or a plurality of set screws (e.g., set screws 200 and/or set screws 202) and/or one or a plurality of spinal rods (e.g., spinal rods 300 and/or spinal rods 302) are employed to augment a surgical treatment. Package 64 can be delivered to an operating room with lid 92 in the closed position. Set screws may be positioned in one or more of cavities 70, 72, 74, 76 and/or with one or a plurality of spinal rods may be positioned within cavity 84, as discussed herein.

Tabs 88, 90 are moved from the second configuration to the first configuration and lid 92 is moved from the closed position to the open position. In some embodiments, sterilized set screws positioned in one or more of cavities 70, 72, 74, 76 and/or one or a plurality of sterilized spinal rods positioned within cavity 84 is/are dumped onto a surface in the operating room, such as, for example, a sterilized surgical tray or table. In some embodiments, one or more sterilized set screw positioned in one or more of cavities 70, 72, 74, 76 is removed from cavities 70, 72, 74, 76 by positioning sterile forceps or other mating instrument, for example, a set screw driver, in one or more of cavities 70, 72, 74, 76 to grasp the set screw therein and remove the set screw from one or more of cavities 70, 72, 74, 76 and/or one or a plurality of sterilized spinal rods positioned within cavity 84 is/are removed from cavity 84 by positioning sterile forceps or other mating instrument, for example, a rod gripper, in cavity 84 to grasp the spinal rod(s) and remove the spinal rod(s) from cavity 84. In some embodiments, the set screw(s) and/or spinal rod(s) is/are transferred from package 64 to a surface in the operating room, such as, for example, a sterilized surgical tray or table using sterile forceps. In some embodiments, the set screw(s) and/or spinal rod(s) is/are engaged with a mating instrument, for example, a set screw driver and/or rod gripper respectively, within package 64 and transferred to the surgeon without the provider touching any components. This prevents contamination of the sterilized setscrew(s) and/or sterilized spinal rod(s). In some embodiments, the sterilized spinal rod(s) is/are removed from cavity 84 as discussed herein and engaged with one or more bone fasteners that have been implanted in vertebrae. A sterilized set screw can then be removed from one or more of cavities 70, 72, 74, 76 as discussed herein and engaged with the bone fastener(s) to fix the spinal rod(s) relative to the bone fastener(s). In some embodiments, package 64 is discarded after the spinal rod(s) and/or set screw(s) are removed from package 64.

Figure 15:
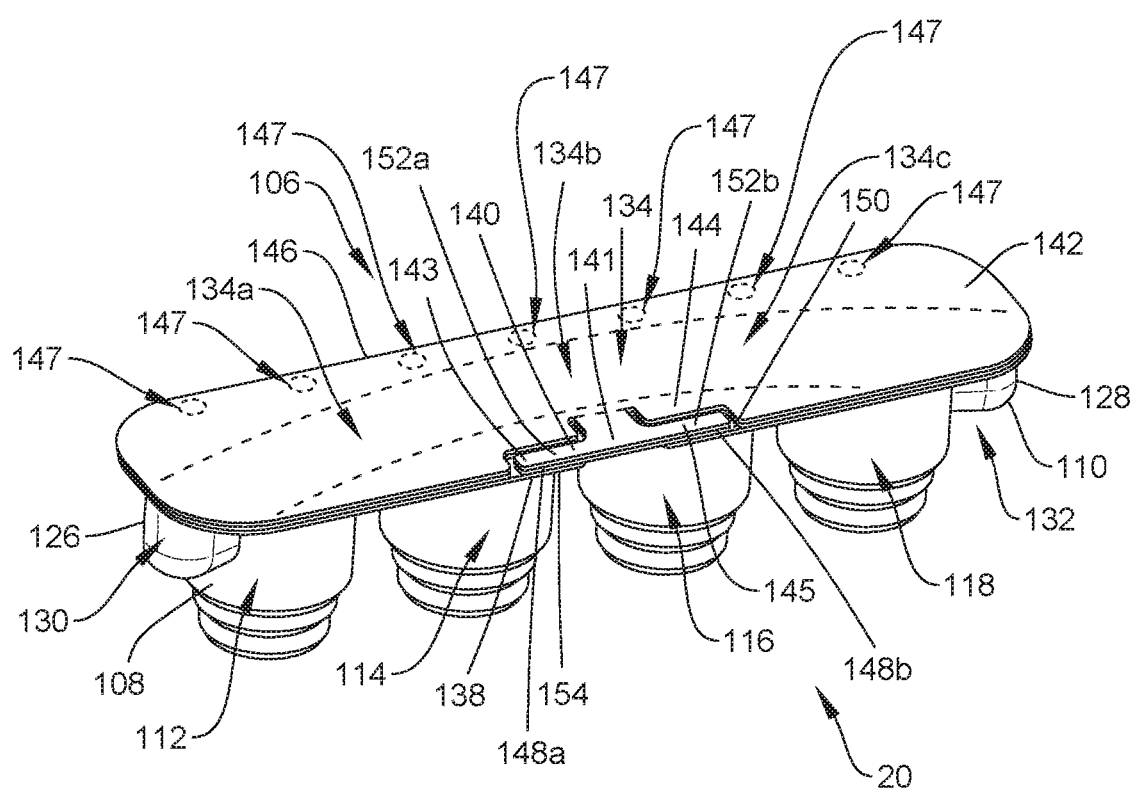
FIG. 15 is a perspective view, in part phantom, of one embodiment of a package, in accordance with principles of the present disclosure.

In one embodiment, shown in FIGS. 15-22, surgical system 20 includes a package 106 that is similar to package 22 and package 64. Package 106 includes a tray 108 comprising a body 110 having pockets, such as, for example, cavities 112, 114, 116, 118. Cavities 112, 114, 116, 118 are each configured for disposal of an implant, such as, for example, set screw 200 and/or set screw 202 (FIGS. 16, 17 and 20-22). Cavity 112 is spaced apart from cavity 114 by a wall 120; cavity 114 is spaced apart from cavity 116 by a wall 122; and cavity 116 is spaced apart from cavity 118 by a wall 124. Body 110 includes an end wall 126 and an opposite end wall 128. Wall 126 defines a recess 130 that is positioned between wall 126 and cavity 122 and wall 128 defines a recess 132 that is positioned between wall 128 and cavity 118. Walls 120, 122, 124 and recesses 130, 132 define a cavity 134 configured for disposal of one or more implants, such as, for example, a spinal rod 300 and/or a spinal rod 302 (FIGS. 18-22), as discussed herein. Cavity 134 extends across cavities 112, 114, 116, 118. Cavity 134 includes a portion 134a between cavities 112, 114, a portion 134b between cavities 114, 116 and a portion 134c between cavities 116, 118. In some embodiments, portions 134a, 134b, 134c and recesses 130, 132 are coaxial to accommodate one or more straight spinal rods in cavity 134. In some embodiments, portions 134a, 134b, 134c each have an equal length. In some embodiments, at least one of portions 134a, 134b, 134c has a length different than the length of another one of portions 134a, 134b, 134c. In some embodiments, portion 134b is linear from cavity 114 to cavity 116. In some embodiments, cavity 134 is continuously curved from wall 126 to wall 128 and/or has a continuous radius of curvature from wall 126 to wall 128, as shown in FIG. 15.

In some embodiments, cavities 112, 114, 116, 118 each have a maximum depth D9 that is greater than a maximum depth D10 of cavity 134, as shown in FIG. 16. As such, bottom portions of cavities 112, 114, 116, 118 are positioned below a bottom portion of cavity 134. This configuration allows one or more spinal rods, such as, for example, spinal rod 300 and/or spinal rod 302 disposed in cavity 134 to be positioned above one or more set screws, such as, for example, set screws 200 and/or set screws 202 that are positioned in one or more of cavities 112, 114, 116, 118 to correspond to the sequence of surgical steps. Indeed, during certain surgical procedures, a spinal rod is engaged with bone fasteners that have been implanted within a patient before set screws are engaged with the bone fasteners to fix the spinal rod to the bone fasteners, as discussed herein. As such, it is preferable to position cavity 134 above cavities 112, 114, 116, 118 so that the spinal rod can be removed from cavity 134 before the set screws are removed from cavities 112, 114, 116, 118 so as to result in an efficient surgical flow.

Figure 21:
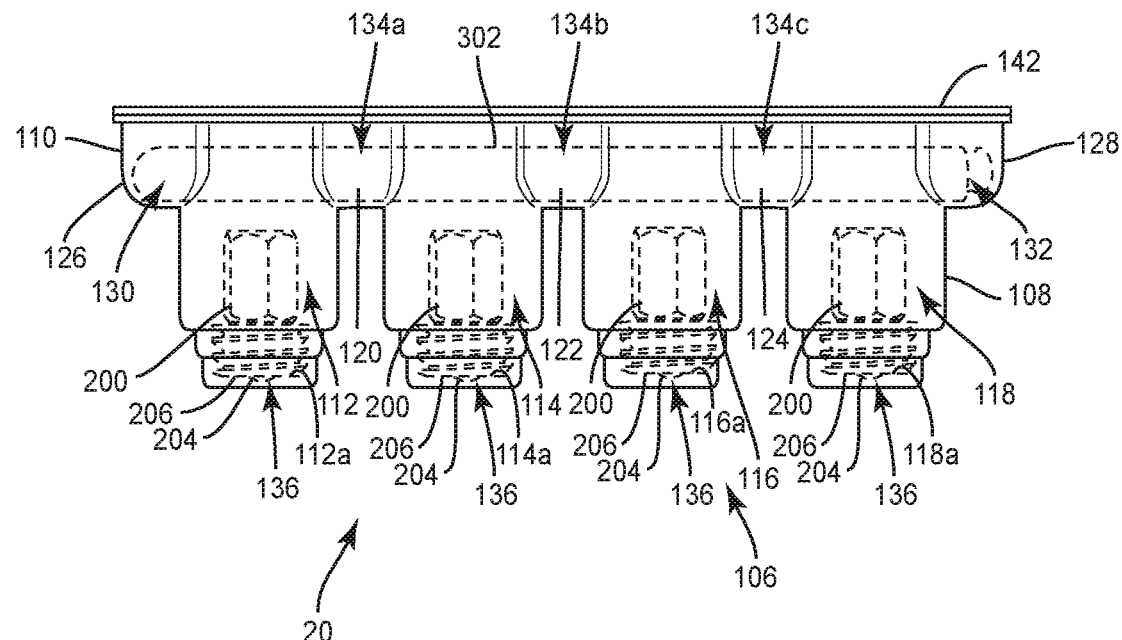
FIG. 21 is a side view, in part phantom, of the package shown in FIG. 15, with a spinal rod and set screws disposed therein.

In some embodiments, cavities 112, 114, 116, 118 each include a recess 136 configured for disposal of dimple 204. When dimple 204 is positioned in recess 136 of cavity 112, surface 206 directly engages a surface 112a of body 110 to maintain set screw 200 in cavity 112 in a manner that prevents movement of set screw 200 within cavity 112, as shown in FIG. 21, for example. When dimple 204 is positioned in recess 136 of cavity 114, surface 206 directly engages a surface 114a of body 110 to maintain set screw 200 in cavity 114 in a manner that prevents movement of set screw 200 within cavity 114. When dimple 204 is positioned in recess 136 of cavity 116, surface 206 directly engages a surface 116a of body 110 to maintain set screw 200 in cavity 116 in a manner that prevents movement of set screw 200 within cavity 116. When dimple 204 is positioned in recess 136 of cavity 118, surface 206 directly engages a surface 136a of body 110 to maintain set screw 200 in cavity 118 in a manner that prevents movement of set screw 200 within cavity 118.

Figure 22:
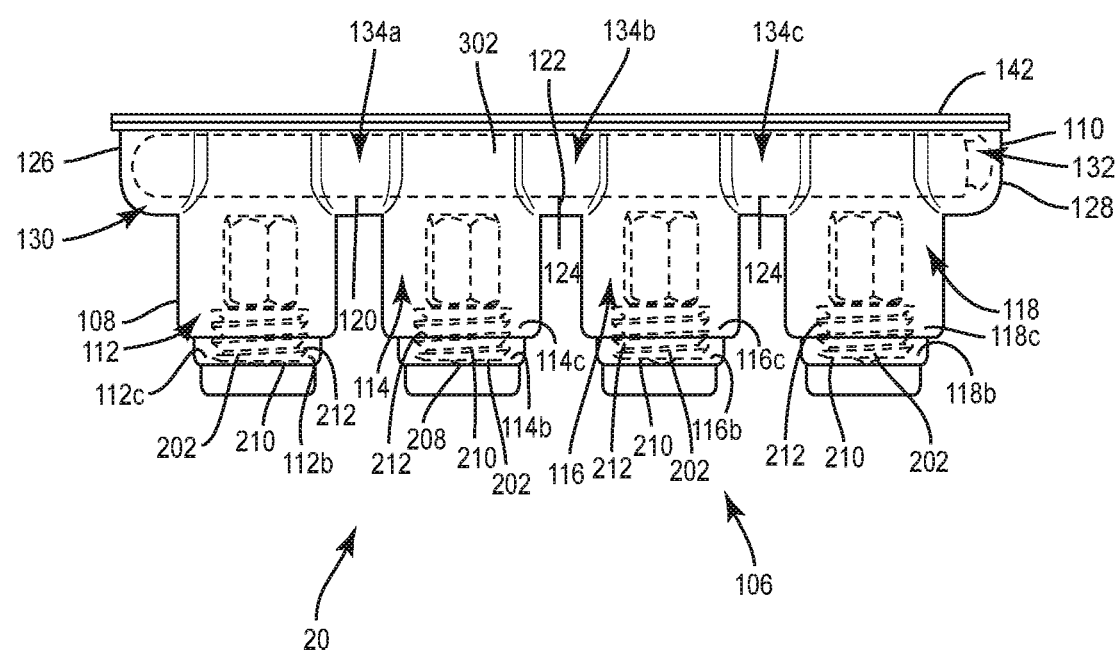
FIG. 22 is a side view, in part phantom, of the package shown in FIG. 15, with a spinal rod and set screws disposed therein.

When set screw 202 is positioned in cavity 112, surface 210 directly engages surface a circumferential flange 112b of body 110 and a side surface 212 of set screw 202 directly engages an inner wall 112c of body 110 to maintain set screw 202 in cavity 112 in a manner that prevents movement of set screw 202 within cavity 112, as shown in FIG. 22, for example. When set screw 202 is positioned in cavity 114, surface 210 directly engages surface a circumferential flange 114b of body 110 and side surface 212 of set screw 202 directly engages an inner wall 114c of body 110 to maintain set screw 202 in cavity 114 in a manner that prevents movement of set screw 202 within cavity 114. When set screw 202 is positioned in cavity 116, surface 210 directly engages surface a circumferential flange 116b of body 110 and side surface 212 of set screw 202 directly engages an inner wall 116c of body 110 to maintain set screw 202 in cavity 116 in a manner that prevents movement of set screw 202 within cavity 116. When set screw 202 is positioned in cavity 118, surface 210 directly engages surface a circumferential flange 118b of body 110 and side surface 212 of set screw 202 directly engages an inner wall 118c of body 110 to maintain set screw 202 in cavity 118 in a manner that prevents movement of set screw 202 within cavity 118.

Package 106, like packages 22, 64, is compatible with multiple implant types, which presents opportunities for various kit combinations all using package 106 to provide a more consistent experience for the customer as well as reducing the amount of packaging and overall cost when kitting multiple implants together. For example, in one embodiment, shown in FIG. 16, set screw 200 is positioned in cavity 112, as discussed herein, and cavities 114, 116, 118, 134 are empty. In one embodiment, shown in FIG. 17, a set screw 200 is positioned in each of cavities 112, 114, 116, 118, as discussed herein, and cavity 134 is empty. In one embodiment, shown in FIG. 18, cavities 112, 114, 116, 118 are empty and rod 300 is positioned in recess 130 and portion 134a of cavity 134, as discussed herein. In one embodiment, shown in FIG. 19, cavities 112, 114, 116, 118 are empty and rod 302 is positioned in recesses 130, 132 and portions 134a, 134b, 134c of cavity 134, as discussed herein. In one embodiment, shown in FIG. 20, cavities 116, 118 are empty, a set screw 200 is positioned in cavities 112, 114, as discussed herein, and rod 300 is positioned in recess 130 and portion 134a of cavity 134, as discussed herein. In one embodiment, shown in FIG. 21, a set screw 200 is positioned in each of cavities 112, 114, 116, 118, as discussed herein, and rod 302 is positioned in recesses 130, 132 and portions 134a, 134b, 134c of cavity 134, as discussed herein. In one embodiment, shown in FIG. 22, a set screw 202 is positioned in each of cavities 112, 114, 116, 118, as discussed herein, and rod 302 is positioned in recesses 130, 132 and portions 134a, 134b, 134c of cavity 134, as discussed herein.

Tray 108 comprises a first wall 138. Wall 138 is configured for engagement with a connecting feature, such as, for example, a tab 140 of a lid 142 of package 106 to secure lid 142 to tray 108 such that lid 142 covers cavities 112, 114, 116, 118, 134, as discussed herein. Tab 140 is movable relative to a body 144 of lid 142. Tab 140 includes a central portion 141, a first flange 143 that extends from a first end of portion 141 and a second flange 145 that extends from a second end of portion 141. Flanges 143, 145 each extend from portion 141 in a cantilevered configuration. Lid 142 is attached to tray 108 by a hinge 146, as best shown in FIG. 15. In some embodiments, hinge 146 is a living hinge. In some embodiments, hinge 146 is a perforated hinge comprising spaced apart points of engagement 147 (FIG. 15) that define portions of package 106 wherein lid 142 is sealed or connected with tray 108. That is, lid 142 is not connected to tray 108 between adjacent points of engagement 147. Lid 142 is rotatable relative to tray 108 about hinge 146 to allow lid 142 to move from a closed position in which lid 142 covers cavities 112, 114, 116, 118, 134 and an open position in which lid 142 does not cover cavities 112, 114, 116, 118, 134. When lid 142 is in the closed position, tab 140 may be manipulated to secure lid 142 to tray 108. In particular, tab 140 is movable relative to wall 138 between a first configuration in which a bottom surface 148a of flange 143 directly engages a top surface 150 of wall 138 and a bottom surface 148b of flange 145 directly engages 150, as shown in FIG. 15, such that lid 142 is rotatable relative to tray 108 about hinge 146 and a second configuration in which a top surface 152a of flange 143 directly engages a bottom surface 154 of wall 138 and a top surface 152b of flange 145 directly engages surface 154 to provisionally fix lid 142 to tray 108 such that rotation of lid 142 relative to tray 108 about hinge 146 is prevented. That is, tab 140 will remain in the second configuration until a force is applied to tab 140 to move tab 140 from the second configuration to the first configuration. When tab 140 is in the first configuration, lid 142 is free to move from the closed position to the open position. Lid 142 is prevented from moving from the closed position to the open position when tab 140 is in the second configuration. In some embodiments, package 106 acts a sterility barrier when lid 142 is in the closed position and/or when tab 140 is in the second configuration that ensures that any implants positioned within package 106 are free from viable microorganisms, for example. That is, sterile implants that are positioned within package 106 will remain sterile when lid 142 is in the closed position and/or tab 140 is in the second configuration.

In assembly, operation and use, surgical system 20 is employed to treat an affected section of vertebrae. The components of surgical system 20 including package 106, one or a plurality of set screws (e.g., set screws 200 and/or set screws 202) and/or one or a plurality of spinal rods (e.g., spinal rods 300 and/or spinal rods 302) are employed to augment a surgical treatment. Package 106 can be delivered to an operating room with lid 142 in the closed position. One or more set screws may be positioned in one or more of cavities 112, 114, 116, 118 and/or one or a plurality of spinal rods may be positioned within cavity 134, as discussed herein.

Tab 140 is moved from the second configuration to the first configuration and lid 142 is moved from the closed position to the open position. In some embodiments, sterilized set screws positioned in one or more of cavities 112, 114, 116, 118 and/or one or a plurality of sterilized spinal rods positioned within cavity 134 is/are dumped onto a surface in the operating room, such as, for example, a sterilized surgical tray or table. In some embodiments, one or more sterilized set screw positioned in one or more of cavities 112, 114, 116, 118 is removed from cavities 112, 114, 116, 118 by positioning sterile forceps or other mating instrument for example, a set screw driver, in cavities 112, 114, 116, 118 to grasp the set screw therein and remove the set screw from one or more of cavities 112, 114, 116, 118 and/or one or a plurality of sterilized spinal rods positioned within cavity 134 is/are removed from cavity 134 by positioning sterile forceps or other mating instrument, for example, a rod gripper, in cavity 134 to grasp the spinal rod(s) and remove the spinal rod(s) from cavity 134. In some embodiments, the set screw(s) and/or spinal rod(s) is/are transferred from package 106 to a surface in the operating room, such as, for example, a sterilized surgical tray or table using sterile forceps. In some embodiments, the set screw(s) and/or spinal rod(s) is/are engaged with a mating instrument, for example, a set screw driver and/or rod gripper respectively, within package 106 and transferred to the surgeon without the provider touching any components. This prevents contamination of the sterilized setscrew(s) and/or sterilized spinal rod(s). In some embodiments, the sterilized spinal rod(s) is/are removed from cavity 134 as discussed herein and engaged with one or more bone fasteners that have been implanted in vertebrae. A sterilized set screw can then be removed from one or more of cavities 112, 114, 116, 118, as discussed herein, and engaged with the bone fastener(s) to fix the spinal rod(s) relative to the bone fastener(s). In some embodiments, package 106 is discarded after the spinal rod(s) and/or set screw(s) are removed from package 106.

Figure 23:
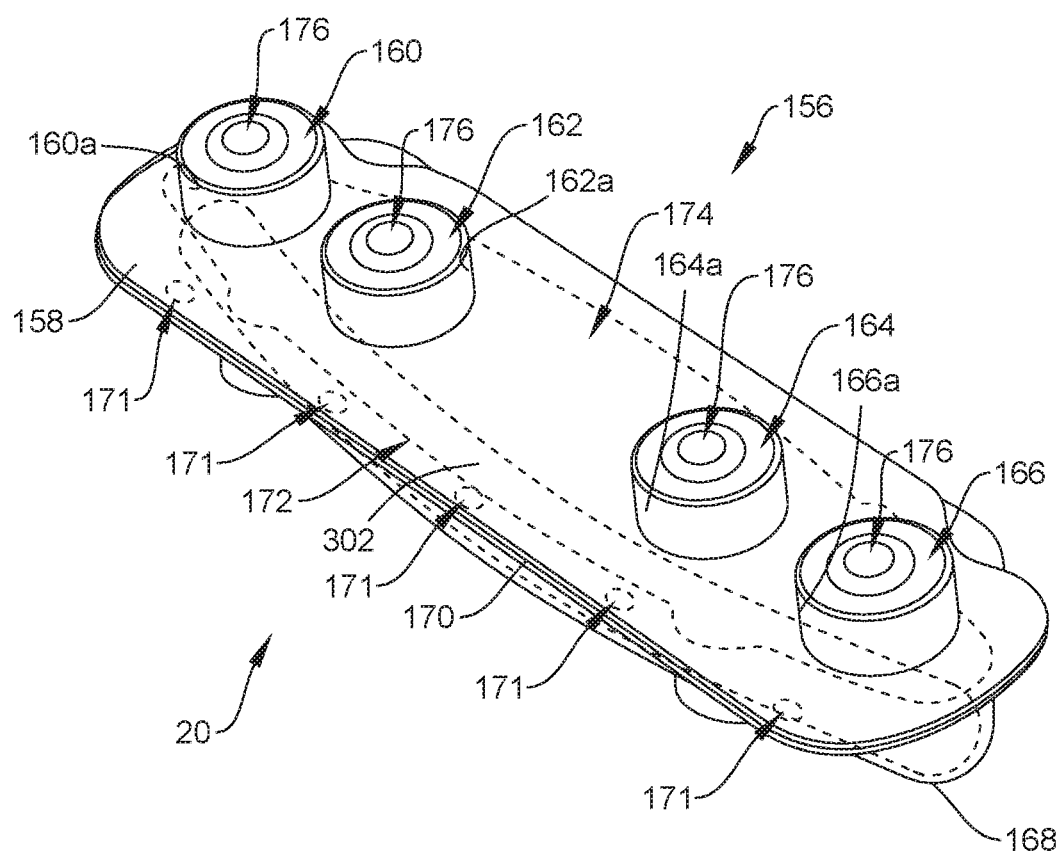
FIG. 23 is a perspective view of one embodiment of a package, in accordance with the present principles of the present disclosure.
Figure 24:
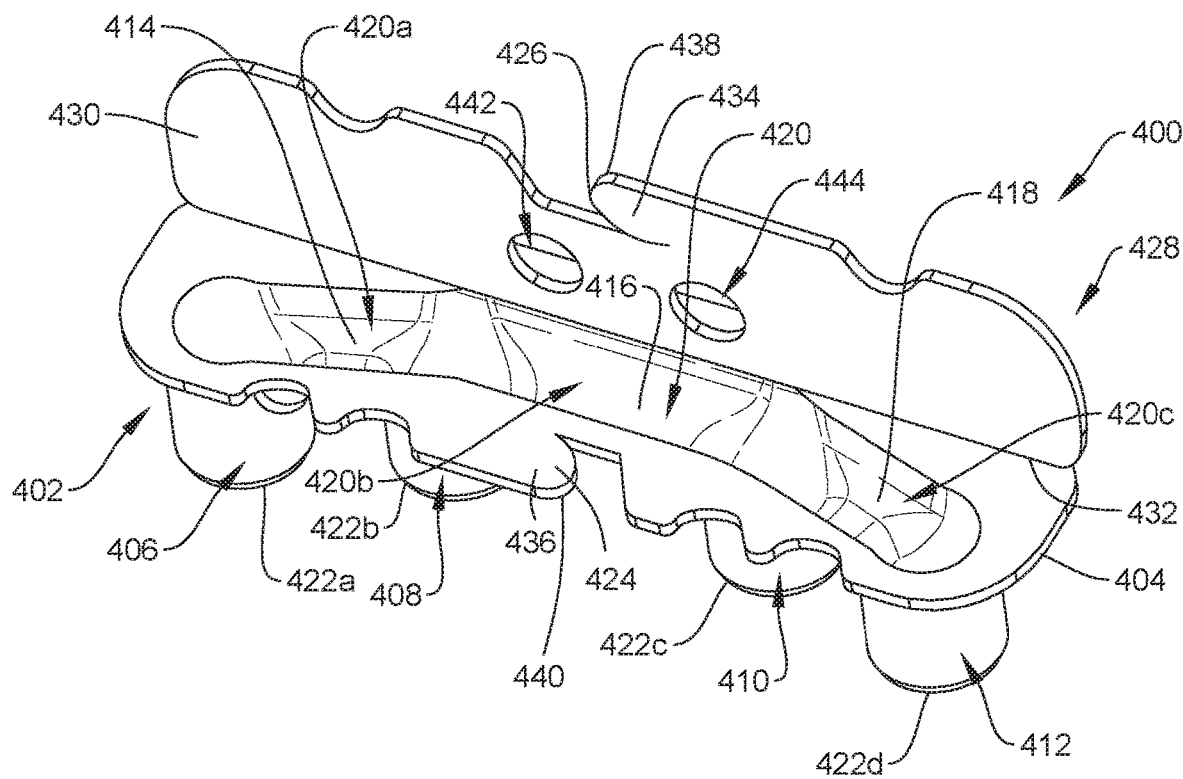
FIG. 24 is a perspective view of one embodiment of a package, in accordance with the present principles of the present disclosure.

In one embodiment, shown in FIG. 23, surgical system 20 includes a package 156 that is similar to packages 24, 64, 106. Package 156 includes a first tray 158 comprising pockets, such as, for example, cavities 160, 162, 164, 166. Cavities 160, 162, 164, 166 are each configured for disposal of an implant, such as, for example, set screw 200 and/or set screw 202 (FIGS. 16, 17 and 20-22). Cavities 160, 162, 164, 166 are spaced apart from one another. A second tray 168 is coupled to tray 158 by a hinge 170 such that tray 158 is rotatable relative to tray 168 about hinge 170. In some embodiments, hinge 170 is a perforated hinge comprising spaced apart points of engagement 171 that define portions of package 156 wherein tray 158 is sealed or connected with tray 168. That is, tray 158 is not connected to tray 168 between adjacent points of engagement 171. Tray 168 includes a cavity 172 and a cavity 174. Cavities 172, 174 are each configured for disposal of an implant, such as, for example, a spinal rod 300 and/or a spinal rod 302 (FIGS. 18-22), as discussed herein. Cavities 172, 174 are continuously curved and/or have a continuous radius of curvature to accommodate pre-bent spinal rods. However, it is envisioned that cavities 172, 174 may be linear to accommodate straight spinal rods.

In some embodiments, cavities 160, 162, 164, 166 each include a recess 176 configured for disposal of dimple 204 and/or dimple 208. When dimple 204 is positioned in recess 176 of cavity 160, surface 206 directly engages a surface 160a of tray 158 to maintain set screw 200 in cavity 160 in a manner that prevents movement of set screw 200 within cavity 160. When dimple 204 is positioned in recess 176 of cavity 162, surface 206 directly engages a surface 162a of tray 158 to maintain set screw 200 in cavity 162 in a manner that prevents movement of set screw 200 within cavity 162. When dimple 204 is positioned in recess 176 of cavity 164, surface 206 directly engages a surface 164a of tray 158 to maintain set screw 200 in cavity 164 in a manner that prevents movement of set screw 200 within cavity 164. When dimple 204 is positioned in recess 176 of cavity 166, surface 206 directly engages a surface 166a of tray 158 to maintain set screw 200 in cavity 166 in a manner that prevents movement of set screw 200 within cavity 166.

When dimple 208 is positioned in recess 176 of cavity 160, surface 210 directly engages a surface 160a of tray 158 to maintain set screw 202 in cavity 160 in a manner that prevents movement of set screw 202 within cavity 160. When dimple 208 is positioned in recess 176 of cavity 162, surface 210 directly engages a surface 162a of tray 158 to maintain set screw 202 in cavity 162 in a manner that prevents movement of set screw 202 within cavity 162. When dimple 208 is positioned in recess 176 of cavity 164, surface 210 directly engages a surface 164a of tray 158 to maintain set screw 202 in cavity 164 in a manner that prevents movement of set screw 202 within cavity 164. When dimple 208 is positioned in recess 176 of cavity 166, surface 210 directly engages a surface 166a of tray 158 to maintain set screw 202 in cavity 166 in a manner that prevents movement of set screw 202 within cavity 166.

Tray 168 is rotatable relative to tray 158 about hinge 170 to allow package 156 to move from a closed position in which tray 158 covers cavities 172, 174 and tray 168 covers cavities 160, 162, 164, 166 and an open position in which tray 158 does not cover cavities 172, 174 and tray 168 does not cover cavities 160, 162, 164, 166. In some embodiments, package 156 acts a sterility barrier when package 156 is in the closed position that ensures that any implants positioned within package 156 are free from viable microorganisms, for example. That is, sterile implants that are positioned within package 156 will remain sterile when package 156 is in the closed position.

In assembly, operation and use, surgical system 20 is employed to treat an affected section of vertebrae. The components of surgical system 20 including package 156, one or a plurality of set screws (e.g., set screws 200 and/or set screws 202) and/or one or a plurality of spinal rods (e.g., spinal rods 300 and/or spinal rods 302) are employed to augment a surgical treatment. Package 156 can be delivered to an operating room with package 156 in the closed position. Set screws may be positioned in one or more of cavities 160, 162, 164, 166 and/or one or a plurality of spinal rods may be positioned within one or more of cavities 172, 174, as discussed herein. Package 156 is moved from the closed position to the open position to provide access to the set screws positioned in one or more of cavities 160, 162, 164, 166 and/or to spinal rods positioned in one or more of cavities 172, 174. The set screw(s) and/or spinal rod(s) may be removed from package 156 using forceps, for example. In some embodiments, the spinal rod(s) is/are engaged with one or more bone fasteners that have been implanted in vertebrae. The set screw(s) is/are then engaged with the bone fastener(s) to fix the spinal rod(s) relative to the bone fastener(s). In some embodiments, package 156 is discarded after the spinal rod(s) and/or set screw(s) are removed from package 156.

Figure 25:
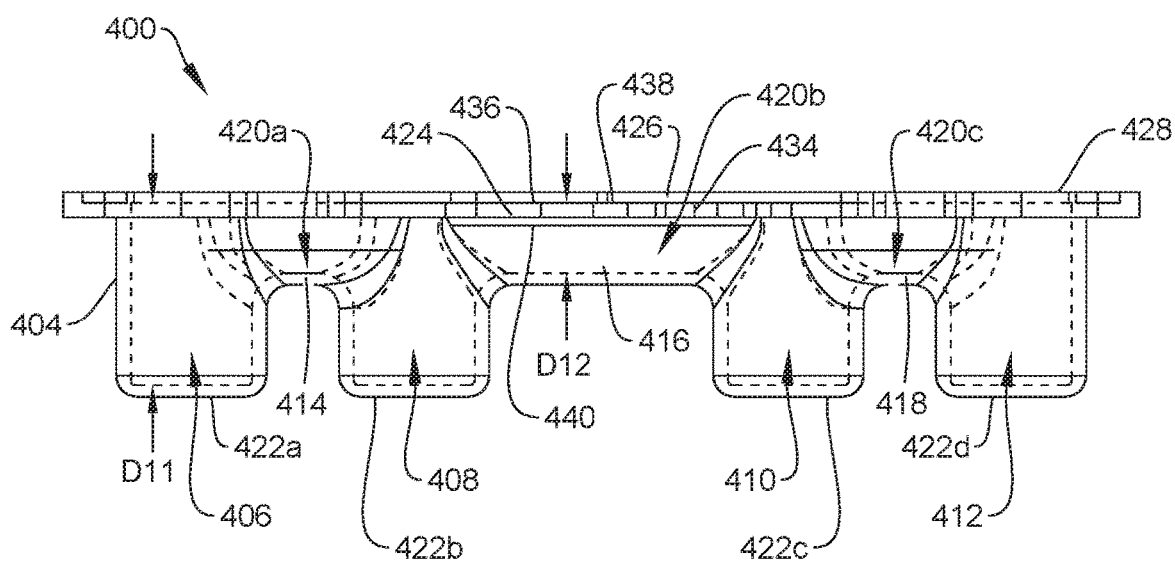
FIG. 25 is a side view, in part phantom, of the package shown in FIG. 24.
Figure 26:
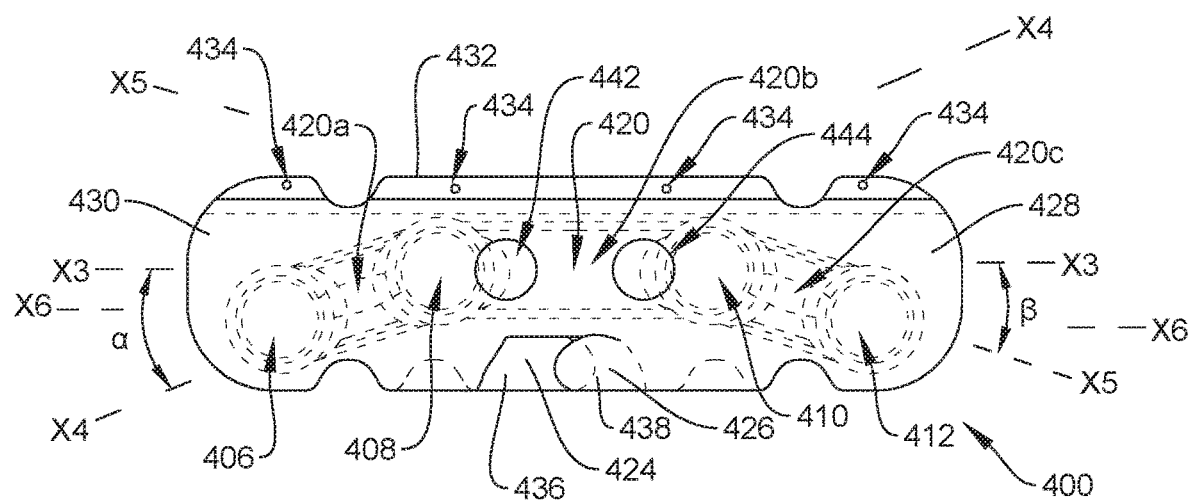
FIG. 26 is a top view, in part phantom, of the package shown in FIG. 24.
Figure 27:
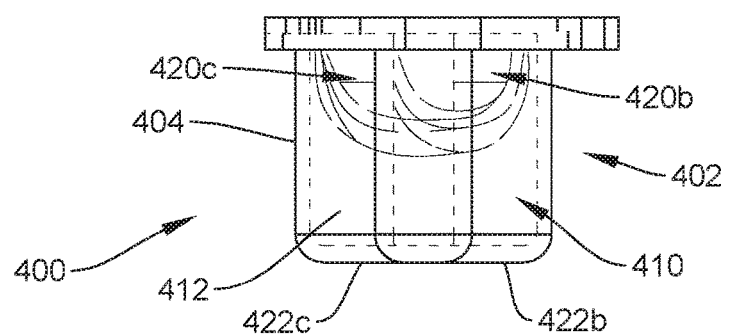
FIG. 27 is an end view, in part phantom, of the package shown in FIG. 24.

In one embodiment, shown in FIGS. 24-28, surgical system 20 includes a package 400 that is similar to packages 24, 64, 106, 156. Package 400 includes a tray 402 comprising a body 404 having pockets, such as, for example, cavities 406, 408, 410, 412. Cavities 406, 408, 410, 412 are each configured for disposal of an implant, such as, for example, set screw 200 and/or set screw 202. Cavity 406 is spaced apart from cavity 408 by a wall 414; cavity 408 is spaced apart from cavity 410 by a wall 416; and cavity 410 is spaced apart from cavity 412 by a wall 418. Walls 414, 416, 418 define a cavity 420 configured for disposal of an implant, such as, for example, spinal rod 300 and/or spinal rod 302, as discussed herein. In some embodiments, cavity 420 is configured for disposal of a pre-bent spinal rod. Cavity 420 extends across cavities 406, 408, 410, 412. Cavity 420 includes a portion 420a between cavities 406, 408, a portion 420b between cavities 408, 410 and a portion 420c between cavities 410, 412. Portion 420b extends along a longitudinal axis X3, portion 420a extends along a longitudinal axis X4 and portion 420c extends along a longitudinal axis X5, as best shown in FIG. 26. Axis X4 extends at an angle α relative to axis X3 and axis X5 extends at an angle β relative to axis X3. In some embodiments, angle α is the same as angle β. In some embodiments, angle α is different than angle β. In some embodiments, angle α is greater than or equal to angle β. In some embodiments, angle α is less than or equal to angle β. In some embodiments, angle α and/or angle β is an acute angle. In some embodiments, angle α and/or angle β is an angle between about 10 degrees and about 80 degrees. In some embodiments, angle α and/or angle β is an angle between about 20 degrees and about 60 degrees. In some embodiments, angle α and/or angle β is an angle between about 20 degrees and about 40 degrees. In some embodiments, portions 420a, 420b, 420c each have an equal length. In some embodiments, portions 420a, 420c each have a length that is less than a length of portion 420b. The configuration of axes X3, X4, X5 results in cavities 408, 410 being aligned along axis X3 and cavities 406, 412 being aligned along an axis X6 that extends parallel to axis. That is, cavities 406, 412 are offset from cavities 408, 410.

In some embodiments, cavities 406, 408, 410, 412 each have a maximum depth D11 that is greater than a maximum depth D12 of cavity 420, as shown in FIG. 25. As such, bottom portions of cavities 406, 408, 410, 412 are positioned below a bottom portion of cavity 420. This configuration allows one or more spinal rods, such as, for example, spinal rod 300 and/or spinal rod 302 disposed in cavity 420 to be positioned above one or more set screws, such as, for example, set screws 200 that are positioned in one or more of cavities 406, 408, 410, 412 to correspond to the sequence of surgical steps. Indeed, during certain surgical procedures, a spinal rod is engaged with bone fasteners that have been implanted within a patient before set screws are engaged with the bone fasteners to fix the spinal rod to the bone fasteners, as discussed herein. As such, it is preferable to position cavity 420 above cavities 406, 408, 410, 412 so that the spinal rod can be removed from cavity 420 before the set screws are removed from cavities 406, 408, 410, 412 so as to result in an efficient surgical flow. In some embodiments, at least one of cavities 406, 408, 410, 412 has a depth that is different than at least another one of cavities 406, 408, 410, 412 to accommodate different size set screws within cavities 406, 408, 410, 412.

In some embodiments, tray 402 includes a bottom wall having a section 422a that defines a portion of cavity 406, a section 422b that defines a portion of cavity 408, a section 422c that defines a portion of cavity 410 and a section 422d that defines a portion of cavity 412. As such, sections 422b, 422c are aligned along axis X3 and sections 422a, 422d are aligned along axis X6 such that sections 422b, 422c are offset from sections 422a, 422d to provide package 400 with a trapezoidal footprint that reduces the chances of package 400 falling over when package 400 is placed on a planar surface, as discussed herein. Sections 422a, 422b, 422c, 422d are planar and extend parallel to one another. In some embodiments, sections 422a, 422b, 422c, 422d are aligned and/or coaxial with one another such that sections 422a, 422b, 422c, 422d define a planar surface configured for placement on a planar surface in an operating room, such as, for example, a surgical table or tray. This configuration allows package 400 to remain upright on the surgical table or tray.

Tray 402 comprises a connecting feature, such as, for example, a first tab 424 that is movable relative to body 404. Tab 424 is configured for engagement with a connecting feature, such as, for example, a second tab 426 of a lid 428 of package 400 to secure lid 428 to tray 402 such that lid 428 covers cavities 406, 408, 410, 412, as discussed herein. Tab 426 is movable relative to a body 430 of lid 428. Lid 428 is attached to tray 402 by a hinge 432. In some embodiments, hinge 432 is a living hinge. In some embodiments, hinge 432 is a perforated hinge comprising spaced apart points of engagement 434 (FIG. 26) that define portions of package 400 wherein lid 428 is sealed or connected with tray 402. That is, lid 428 is not connected to tray 402 between adjacent points of engagement 434.

Lid 428 is rotatable relative to tray 402 about hinge 432 to allow lid 428 to move from a closed position in which lid 428 covers cavities 406, 408, 410, 412 and an open position in which lid 428 does not cover cavities 406, 408, 410, 412. When lid 428 is in the closed position, tabs 424, 426 may be manipulated to secure lid 428 to tray 402. In particular, tab 426 is movable relative to tab 424 between a first configuration in which a bottom surface 434 of tab 426 directly engages a top surface 436 of tab 424 such that lid 428 is rotatable relative to tray 402 about hinge 432 and a second configuration in which a top surface 438 of tab 426 directly engages a bottom surface 440 of tab 424 to provisionally fix lid 428 to tray 402 such that rotation of lid 428 relative to tray 402 about hinge 432 is prevented. That is, tabs 424, 426 will remain in the second configuration until a force is applied to tab 424 and/or tab 426 to move tabs 424, 426 from the second configuration to the first configuration. When tabs 424, 426 are in the first configuration, lid 428 is free to move from the closed position to the open position. Lid 428 is prevented from moving from the closed position to the open position when tabs 424, 426 are in the second configuration. In some embodiments, lid 428 includes a first through-cut 442 and a second through-cut 444 that is spaced apart from through-cut 442. Through-cuts 442, 444 extend through a thickness of lid 428 and are configured for disposal of portions of an instrument, such as, for example, forceps F to move tabs 424, 426 between the first and second configurations, as discussed herein. In some embodiments, through-cut 442 and/or through-cut 444 can be variously shaped, such as, for example, circular, oval, oblong, triangular, square, polygonal, irregular, uniform, non-uniform, offset, staggered, undulating, arcuate, variable and/or tapered.

Figure 28:
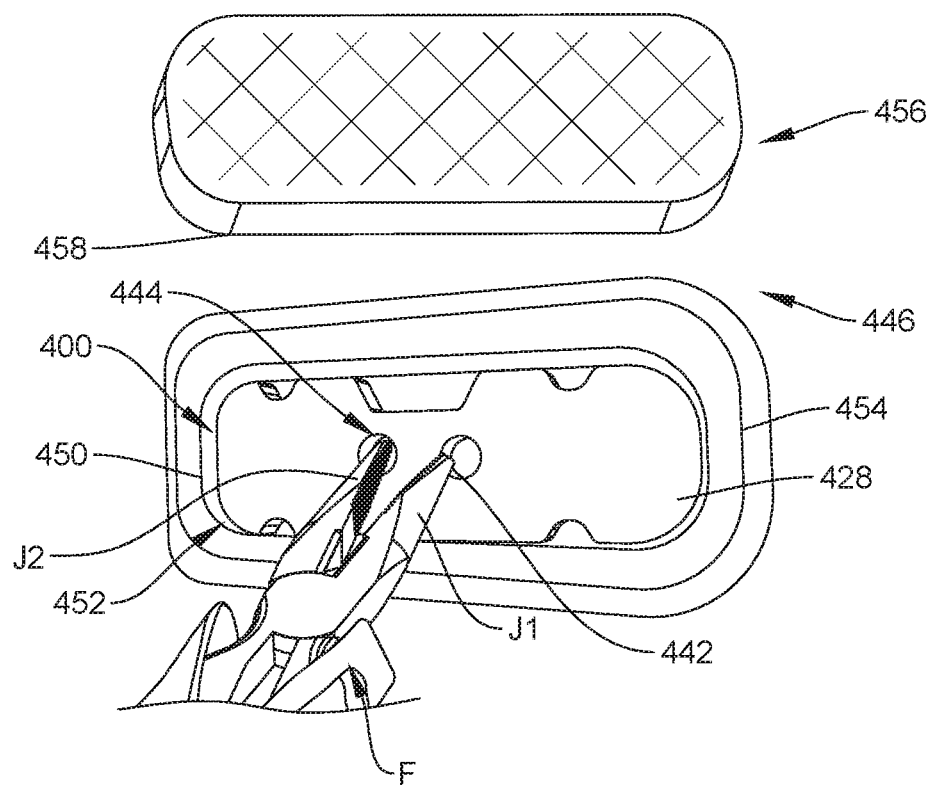
FIG. 28 is a perspective view of the package shown in FIG. 24, with the package positioned in a tray.

In assembly, operation and use, surgical system 20 is employed to treat an affected section of vertebrae. The components of surgical system 20 including package 400, one or a plurality of set screws (e.g., set screws 200 and/or set screws 202) and/or one or a plurality of spinal rods (e.g., spinal rods 300 and/or spinal rods 302) are employed to augment a surgical treatment. Package 400 can be delivered to an operating room with lid 428 in the closed position. Set screws may be positioned in one or more of cavities 406, 408, 410, 412 and/or one or a plurality of spinal rods may be positioned within cavity 420, as discussed herein. Tabs 424, 426 are moved from the second configuration to the first configuration and lid 428 is moved from the closed position to the open position. In some embodiments, lid 428 is gripped by forceps F by positioning a first jaw J1 of forceps F into through-cut 442 and positioning a second jaw J2 of forceps F into through-cut 44, as shown in FIG. 28. Forceps F are then manipulated to rotate lid 428 relative to tray 402 to move lid 428 from the closed position to the open position. In some embodiments, sterilized set screws positioned in one or more of cavities 406, 408, 410, 412 and/or one or a plurality of sterilized spinal rods positioned within cavity 420 is/are dumped onto a surface in the operating room, such as, for example, a sterilized surgical tray or table. In some embodiments, one or more sterilized set screw positioned in one or more of cavities 406, 408, 410, 412 is removed from cavities 406, 408, 410, 412 by positioning sterile forceps or other mating instrument, for example, a set screw driver, in one or more of cavities 406, 408, 410, 412 to grasp the set screw therein and remove the set screw from one or more of cavities 406, 408, 410, 412 and/or one or a plurality of sterilized spinal rods positioned within cavity 420 is/are removed from cavity 420 by positioning sterile forceps or other mating instrument, for example, a rod gripper, in cavity 420 to grasp the spinal rod(s) and remove the spinal rod(s) from cavity 420. In some embodiments, the set screw(s) and/or spinal rod(s) is/are transferred from package 400 to a surface in the operating room, such as, for example, a sterilized surgical tray or table using sterile forceps. In some embodiments, the set screw(s) and/or spinal rod(s) is/are engaged with a mating instrument, for example, a set screw driver and/or rod gripper respectively, within package 400 and transferred to the surgeon without the provider touching any components. This prevents contamination of the sterilized setscrew(s) and/or sterilized spinal rod(s). In some embodiments, the sterilized spinal rod(s) is/are removed from cavity 400 as discussed herein and engaged with one or more bone fasteners that have been implanted in vertebrae. A sterilized set screw can then be removed from one or more of cavities 406, 408, 410, 412 as discussed herein and engaged with the bone fastener(s) to fix the spinal rod(s) relative to the bone fastener(s). In some embodiments, package 400 is discarded after the spinal rod(s) and/or set screw(s) are removed from package 400.

In embodiments of package 400 wherein lid 428 includes through-cuts 442, 444, package 400 does not provide a sterility barrier even when lid 428 is in the closed position and/or when tabs 424, 426 are in the second configuration. Indeed, it is envisioned that viable microorganisms can move through through-cut 442 and/or through-cut 444 and into one or more of cavities 406, 408, 410, 412, 420 and hence compromise the sterility of any implants that are positioned in cavities 406, 408, 410, 412, 420. Accordingly, in some embodiments, system 20 can include an external container, as shown in FIG. 28. Container 446 includes a base 448 having a wall 450 that defines a cavity 452 configured for disposal of package 400. Base 448 includes a flange 454 that extends from wall 450. Container 446 includes a cover 456 having a bottom surface 458 that is configured to directly engage flange 454 to enclose package 400 within cavity 452. Cover 456 has a solid wall configuration that is free of any gaps, apertures, or recesses. In some embodiments, container 446 acts a sterility barrier when cover 456 engages flange 454 and ensures that package 400 and/or any implants positioned within package 400 are free from viable microorganisms, for example. That is, package 400 and/or sterile implants that are positioned within package 400 will remain sterile when cover 456 engages flange 454.

In some embodiments, a kit containing one or more components of surgical system 20 is provided. The kit may comprise components from any of the embodiments discussed herein. In some embodiments, the kit comprises one or more of packages 22, 64, 106, 156, 400. In some embodiments, the kit comprises one or more bone fasteners, such as, for example, one or more of the bone fasteners discussed herein. In some embodiments, the kit comprises one or spinal rods, such as, for example, spinal rods having different lengths, straight spinal rods, pre-bent spinal rods and/or spinal rods made from different materials. In some embodiments, the kit comprises a plurality of set screws, such as, for example, different size set screws and/or set screws made from different materials. In some embodiments, the kit comprises one or a plurality of instruments, such as, for example, forceps to remove implants from the packages. In some embodiments, the kit comprises one or a plurality of instruments to implant the implants, such as, for example, one or more rod inserters and/or drivers.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant package comprising:
a tray comprising a body having spaced apart first and second cavities, the body comprising a third cavity between the first and second cavities, the first and second cavities each being configured for disposal of a set screw, the first and second cavities each having a first depth and the third cavity having a second depth, the second depth being less than the first depth, the tray comprising a first connecting feature, the first connecting feature being movable relative to the body, the body comprising a wall, the wall including the first connecting feature, the wall comprising a first end adjacent to the first cavity and an opposite second end adjacent to the second cavity, the first end defining opposite first and second cut-outs and the second end defining opposite third and fourth cut-outs, the cut-outs each extending into an outer surface of the wall; and
a lid coupled to the tray by a hinge, the lid comprising a second connecting feature, the second connecting feature being movable between a first position in which a bottom surface of the second connecting feature directly engages a top surface of the first connecting feature and a second position in which a top surface of the second connecting feature directly engages a bottom surface of the first connecting feature to provisionally fix the lid to the tray.

2. The package recited in claim 1, wherein the third cavity is configured for disposal of a spinal rod.

3. The package recited in claim 1, wherein the third cavity extends between opposite first and second ends, the third cavity having a generally elongated shape from the first end to the second end.

4. The package recited in claim 1, wherein the third cavity extends between opposite first and second ends, the third cavity having an arcuate shape from the first end to the second end.

5. The package recited in claim 1, wherein the third cavity includes a first section having a first dimension, for accommodating a rod body, and a second portion having a second dimension, wherein the second dimension is larger than the first dimension, for accommodating a rod end cap that larger in a dimension than the rod body.

6. The package recited in claim 1, wherein the hinge is perforated.

7. The package recited in claim 1, wherein the third cavity is in communication with the first cavity and the second cavity.

8. The package recited in claim 1, wherein the third cavity includes a first end in communication with the first cavity and an opposite second end in communication with the second cavity.

9. The package recited in claim 1, wherein the third cavity is in communication with the first cavity and the second cavity such that the first and second cavities are positioned below the third cavity.

10. The package recited in claim 1, wherein the third cavity comprises a first end portion, a second end portion and an intermediate portion between the end portions, the intermediate portion having a diameter less than diameters of the end portions.

11. The package recited in claim 1, wherein the third cavity comprises a first end portion in communication with the first cavity and a second end portion in communication with the second cavity, the third cavity comprising an intermediate portion between the end portions, the intermediate portion having a diameter less than diameters of the end portions.

12. The package recited in claim 1, wherein the third cavity comprises a first end portion in communication with the first cavity and a second end portion in communication with the second cavity, the third cavity comprising an intermediate portion between the end portions, the intermediate portion being continuously curved from the first end portion to the second end portion.

13. The package recited in claim 1, wherein the third cavity comprises a first end portion in communication with the first cavity and a second end portion in communication with the second cavity, the third cavity comprising an intermediate portion between the end portions, the third cavity being tapered from the first end portion to the intermediate portion and from the second end portion to the intermediate portion.

14. The package recited in claim 1, wherein the outer surface of the wall defines a perimeter of the tray.

15. The package recited in claim 1, wherein the outer surface is continuously curved from the first cut-out to the second cut-out and is continuously curved from the third cut-out to the fourth cut-out.

16. The package recited in claim 1, wherein the first connecting feature is positioned between the first cut-out and the third cut-out.

17. The package recited in claim 1, wherein the cut-outs are each positioned between the first cavity and the second cavity.

18. A spinal implant package comprising:
a tray comprising a body having spaced apart first and second cavities, the body comprising a third cavity between the first and second cavities, the third cavity being in communication with the first cavity and the second cavity such that the bottoms of the first and second cavities are positioned below a bottom of the third cavity, the third cavity comprising a first end portion in communication with the first cavity and a second end portion in communication with the second cavity, the third cavity comprising an intermediate portion between the end portions, the intermediate portion being continuously curved from the first end portion to the second end portion, the tray comprising a first connecting feature, the first connecting feature being movable relative to the body; and
a lid coupled to the tray by a hinge, the lid comprising a second connecting feature, the second connecting feature being movable between a first position in which a bottom surface of the second connecting feature directly engages a top surface of the first connecting feature and a second position in which a top surface of the second connecting feature directly engages a bottom surface of the first connecting feature to provisionally fix the lid to the tray.

19. A spinal implant package comprising:
a tray comprising a body having spaced apart first and second cavities, the body comprising a third cavity between the first and second cavities, the tray comprising a first connecting feature, the first connecting feature being movable relative to the body,
the body comprising a wall, the wall including the first connecting feature, the wall comprising a first end adjacent to the first cavity and an opposite second end adjacent to the second cavity, the first end defining opposite first and second cut-outs and the second end defining opposite third and fourth cut-outs, the cut-outs each extending into an outer surface of the wall, the outer surface being continuously curved from the first cut-out to the second cut-out and continuously curved from the third cut-out to the fourth cut-out; and
a lid coupled to the tray by a hinge, the lid comprising a second connecting feature, the second connecting feature being movable between a first position in which a bottom surface of the second connecting feature directly engages a top surface of the first connecting feature and a second position in which a top surface of the second connecting feature directly engages a bottom surface of the first connecting feature to provisionally fix the lid to the tray.

* * * * *